(12) United States Patent
Class et al.

(10) Patent No.: US 6,884,423 B1
(45) Date of Patent: Apr. 26, 2005

(54) ANTIMICROBIAL HISTONE H1 COMPOSITIONS, KITS, AND METHODS OF USE THEREOF

(75) Inventors: Reiner Class, Saarlouis (DE); Michael Zeppezauer, Saarbrüken/Scheidt (DE)

(73) Assignees: Symbiotec GmbH, Saarbrücken (DE); Philadelphia Health and Education Corporation, Philadelphia, PA (US)

( * ) Notice: Subject to any disclaimer, the term of this patent is extended or adjusted under 35 U.S.C. 154(b) by 0 days.

(21) Appl. No.: 10/049,753

(22) PCT Filed: Aug. 9, 2000

(86) PCT No.: PCT/US00/21747

§ 371 (c)(1), (2), (4) Date: Oct. 10, 2002

(87) PCT Pub. No.: WO01/10901

PCT Pub. Date: Feb. 15, 2001

Related U.S. Application Data

(63) Continuation-in-part of application No. 09/372,500, filed on Aug. 11, 1999, now Pat. No. 6,565,854.
(60) Provisional application No. 60/096,382, filed on Aug. 13, 1998.

(51) Int. Cl.[7] .................. A61K 36/02; A61K 49/00; A61K 38/16; C12P 21/04
(52) U.S. Cl. .................. 424/234.1; 424/9.2; 424/78.07; 424/902; 435/71.3; 530/358; 930/130
(58) Field of Search .................. 424/9.2, 78.07, 424/234.1, 902; 435/71.3; 530/358; 930/190

(56) References Cited

U.S. PATENT DOCUMENTS

| | | | |
|---|---|---|---|
| 5,182,257 A | * | 1/1993 | Zeppezauer et al. .......... 514/2 |
| 5,578,571 A | * | 11/1996 | Zeppezauer et al. .......... 514/12 |
| 5,780,432 A | | 7/1998 | Zeppezauer |

FOREIGN PATENT DOCUMENTS

| | | |
|---|---|---|
| EP | 0 392 315 A1 | 10/1990 |
| GB | 563 651 A | 8/1944 |
| WO | WO 97 38713 A1 | 10/1997 |
| WO | WO 99 37318 A1 | 7/1999 |

OTHER PUBLICATIONS

Ashmarin et al., 1971, & Dokl. Akad. Nauk SSSR, 201(2), 477–9 (abstract only).
Ashmarin et al., 1972, & Antibiotiki 17(3), 266–9 (abstract only).
Gerchman et al., 1994, Prot. Express. Purif. 5:242–251.
Hirsch, J.G., J. Experimental Med., JP, vol. 108, pp. 925–944, 1958.
Hoffert, 1998, The Scientist 12:6.
Isenberg, 1979, Annu. Rev. Biochem. 48:159–191.
Linder et al., 1994, Mol. Cell. Biol. 4:2822–2835.
Murray, 1977, Am. J. Med. 102:284–293.
Pehrson et al., 1981, Biochemistry 20:2298–2301.
Rose et al., 1998, Infection and Immunity 66:3255–3263.
Roth et al., 1997, Appl. Env. Microbiol. 63:2421–2431.

* cited by examiner

*Primary Examiner*—Rodney P Swartz
(74) *Attorney, Agent, or Firm*—Akin Gump Strauss Hauer & Feld, LLP

(57) ABSTRACT

The invention includes antibiotic pharmaceutical compositions comprising eukaryotic histone H1 protein and methods of using eukaryotic histone H1 protein to kill or to inhibit the growth of microorganisms, including, but not limited to, human pathogenic bacteria. The invention further includes a eukaryotic histone H1-containing animal feed and methods of improving growth of an animal by supplying the feed to the animal. The invention still further includes a kit comprising a eukaryotic histone H1-containing antibiotic pharmaceutical composition and an instructional material which describes the use of the composition. In addition, the invention includes a vaccine comprising a eukaryotic histone H1 protein and a method of vaccinating an animal using the vaccine.

37 Claims, 9 Drawing Sheets

ANTIMICROBIAL HISTONE H1 COMPOSITIONS, KITS, AND METHODS OF USE THEREOF

CROSS-REFERENCE TO RELATED APPLICATIONS

This application is a 371 of PCT/US00/21747 filed Aug. 9, 2000, which is a continuation-in-part of Ser. No. 09/372,500 filed Aug. 11, 1999, now U.S. Patent 6,565,854 B2, issued May 20, 2003, which in turn claims the benefit of priority of U.S. Provisional Patent Application No. 60/096,382, filed Aug. 13, 1998.

FIELD OF THE INVENTION

The field of the invention is antibiotic compositions, kits, and methods of use thereof.

BACKGROUND OF THE INVENTION

Numerous antibiotic compositions are known, some exhibiting antibiotic activity against a broad spectrum of microorganisms, and others exhibiting antibiotic activity only against one or a few narrow classes of organisms, such as gram-positive bacteria. One shortcoming associated with all known antibiotics is that microorganisms, especially bacteria, can become resistant to an antibiotic to which they were previously susceptible under certain conditions. Human pathogens are among the microorganisms which are capable of developing antibiotic resistance. Thus, even though certain antibiotics are highly efficacious against a broad range of microorganisms, it is necessary to continually develop new antibiotic compositions in order to remain ahead of the development of antibiotic-resistant microorganisms or to develop antibiotics that are, due to their intrinsic characteristics of antimicrobial action, less likely to generate resistant strains. Further, the continuing identification of new antibiotics will reduce the likelihood that a strain of microorganism will arise which is resistant to most or all known antibiotics.

Bacterial resistance to antibiotics is an increasing problem of potentially pandemic proportions, both in the United States and abroad. In one review, more than 31% of 17,000 bacterial isolates of *Streptococcus pneumoniae* obtained from patients were identified as being resistant to penicillin. Furthermore, in 1997, three untreatable vancomycin-resistant cases were reported in Camden, N.J. (Murray, 1977, Am. J. Med. 102:284–293).

The need for anti-microbial products has increased in the past few years, due to the emergence of multi-drug resistant bacterial infections. The U.S. Centers for Disease Control and Prevention estimate that antibiotics are one of the most widely used classes of drugs, both in the United States and world-wide. Extensive research efforts are underway to identify potential antibiotic candidate compounds. The present invention satisfies the continuing need for new antibiotic compositions.

BRIEF SUMMARY OF THE INVENTION

The invention relates to a method of inducing death of a microorganism. The method comprises contacting the microorganism with a composition comprising a substantially purified eukaryotic histone H1 protein. Death of the microorganism is thereby induced. In one embodiment the microorganism is a human pathogen such as a bacterium selected from the group consisting of *Escherichia coli*, *Klebsiella pneumoniae*, a *Shigella* species, *Serratia marcescens*, *Bacillus cereus*, *Bacillus subtilis*, *Pseudomonas aeruginosa*, *Proteus morgani*, *Staphylococcus albus*, *Salmonella typhimurium*, *Salmonella enteritidis*, and *Bacillus megaterium*. In another embodiment, the eukaryotic histone H1 protein is chemically modified, such as a polyethylene glycol-derivated eukaryotic histone H1 protein.

The invention also relates to a method of inhibiting growth of a microorganism. This method comprises contacting the microorganism with a composition comprising a substantially purified eukaryotic histone H1 protein.

The invention further relates to an antimicrobial pharmaceutical composition comprising a substantially purified eukaryotic histone H1 protein and a pharmaceutically acceptable carrier. The composition may, for example, be in the form of a suspension suitable for injection or infusion into an animal tissue, such as blood. The composition may also be, for example, in the form of a wound dressing.

The wound dressing may be selected from the group consisting of a creme, a gel, an absorbent material, and a physiologically degradable material. In one embodiment, the composition further comprises a supplemental antibiotic, such as one selected from the group consisting of histones H2A, H2B, H3, H4, and H5, penicillin, streptomycin, vancomycin, bacitracin, polymyxin, neomycin, chloramphenicol, chlortetracycline, ciprofloxacin, tobramycin, erythromycin, gentamicin, gramicidin, oxytetracycline, norfloxacin, a salt of an antibiotic, and an ester of an antibiotic.

The invention still further relates to a kit comprising the composition of the invention and an instructional material selected from the group consisting of an instructional material which describes use of the antimicrobial composition to kill a microorganism and an instructional material which describes use of the antimicrobial composition to arrest the growth of a microorganism. The composition may, for example, be in a unit dosage form. In one embodiment, the kit further comprises a histone H1 antidote such as heparin.

The invention also relates to a method of treating a microbial infection in an animal. This method comprises administering an antimicrobial composition comprising a substantially purified eukaryotic histone H1 protein to the animal. The animal may be a mammal such as a human. Furthermore, the composition may, for example, be administered to the animal by a route selected from the group consisting of an oral route, an intraperitoneal route, an intravenous route, and a topical route.

The invention further relates to a method of inhibiting microbial growth at a site. This method comprises providing an antimicrobial composition comprising a eukaryotic histone H1 protein to the site. The composition may be provided at the site by incorporating the composition into the site, for example. In various embodiments, the site is located on or within a foodstuff or on or within an animal tissue. In other embodiments, the composition is provided to an animal tissue during a surgical procedure or to a site by providing the composition to a surface which contacts the site. The surface may, for example, be selected from the group consisting of a surface of a wound of an animal and a surface of a surgical implement. In another embodiment, the site is an internal portion of an animal and wherein the composition is provided to the site by providing a biodegradable implant comprising the composition to the site.

The invention still further relates to a supplemented animal feed comprising an animal feed supplemented with an antimicrobial composition comprising a substantially purified eukaryotic histone H1 protein.

In addition, the invention relates to a method of improving growth of a non-human animal. This method comprising feeding the animal the supplemented animal feed of the invention. The non-human animal may, for example, be a farm animal.

The invention also relates to a method of preparing an animal vaccine. This method comprises adding a eukaryotic histone H1 protein to a preparation of a microorganism. The microorganism is thereby killed, and the preparation of the killed microorganism comprises the vaccine.

The invention further relates to a method of vaccinating an animal, the method comprising administering to the animal the vaccine of the invention.

The invention still further relates to another method of vaccinating an animal. This method comprising administering to the animal a composition comprising an attenuated or killed form of a microorganism and a substantially purified eukaryotic histone H1 protein.

DETAILED DESCRIPTION

Figure 1:
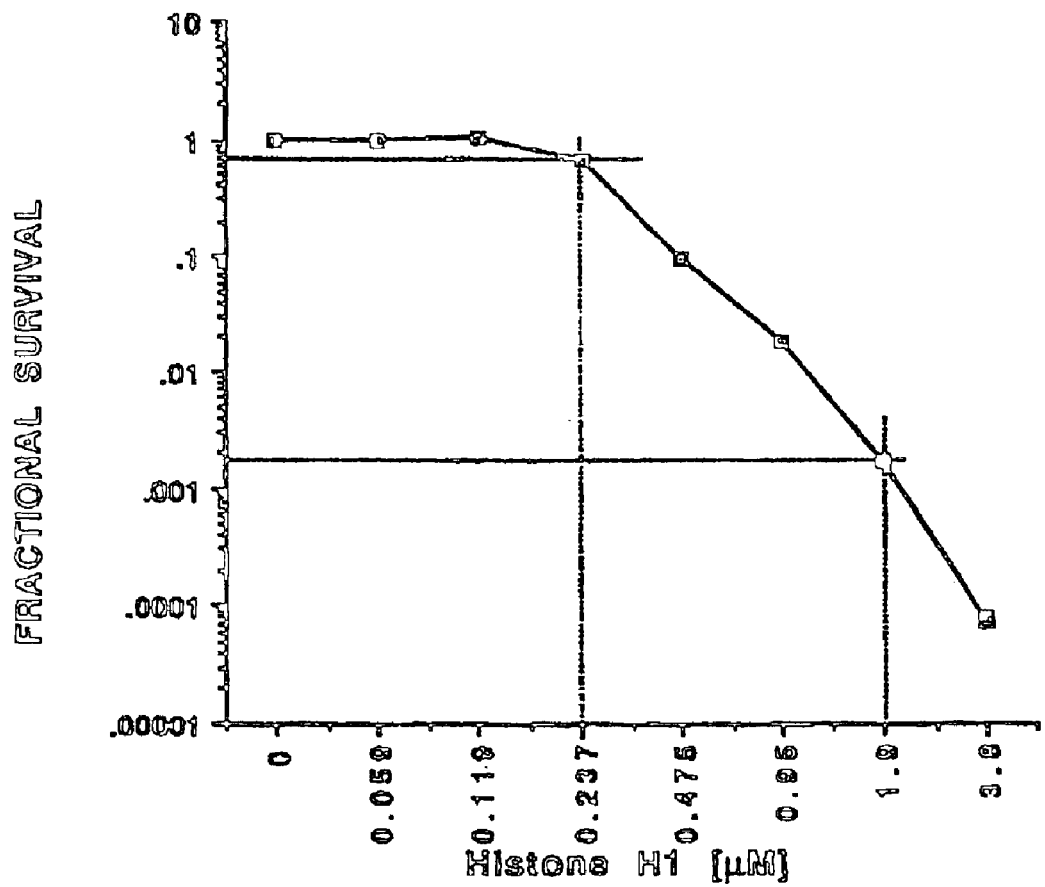
FIG. 1 is a graph which indicates the concentration dependence of the antibiotic activity exhibited by histone H1 with respect to *E. coli* strain AB1157.

The invention is based on the discovery that eukaryotic histone H1 protein exhibits antibiotic activity. The invention thus relates to antibiotic compositions comprising a eukaryotic histone H1 protein. The invention also relates to methods of killing a microorganism and preventing or reducing the growth of a microorganism, the methods comprising contacting the microorganism with a eukaryotic histone H1 protein.

As used herein, an "antibiotic" is a chemical substance which exhibits antibiotic activity.

As used herein, a chemical substance exhibits "antibiotic activity" if the substance leads to the death of or inhibits or prevents growth of a microorganism with which it is contacted.

As used herein, a chemical substance "inhibits growth of a microorganism" if the substance decreases the rate of increase of the cell number or the size of the microorganism, decreases the rate of proliferation of the microorganism, or prevents the growth of the microorganism.

As used herein, a "microorganism" means an organism of microscopic dimensions, including both single-celled and multicellular organisms. Generally speaking, microorganisms are not larger than about 250 micrometers along their longest dimension, it being understood that some microorganisms exist in extended multicellular complexes having significantly larger dimensions. Multicellular complexes of microorganisms do not comprise tissues having specialized cell types, and such complexes may therefore be differentiated from similarly-sized organisms which are not microorganisms and which comprise tissues having specialized cell types. Microorganisms therefore include, but are not limited to, protozoa, algae, fungi, molds, bacteria, and archaea.

Toxic concentrations of eukaryotic Histone H1 depend on the cell type being treated. The toxic concentration of Histone H1 for most non-cancerous eukaryotic cells is more than about 200 or 250 micrograms per milliliter. The toxic concentration of Histone H1 for eukaryotic tumor cells is about 150 to 200 micrograms per milliliter. The toxic concentration of Histone H1 for bacterial cells is less than about 80 micrograms per milliliter.

As used herein, a "bactericidal" agent is a chemical substance which leads to the death of a bacterium with which it is contacted.

As used herein, a "bacteriostatic" agent is a chemical substance which inhibits the growth of a bacterium with which it is contacted.

As used herein, a microorganism exhibits "antibiotic resistance" if a chemical substance which exhibits antibiotic activity with respect to a naturally-occurring form of the microorganism is ineffective against the microorganism.

Compositions Comprising Eukaryotic Histone H1

Histone H1 is a protein which has a size and an amino acid sequence that are highly conserved among eukaryotic organisms. Several eukaryotic organisms, including humans for example, comprise a plurality of subtypes of histone H1 which share a high degree of homology. Histone H1 comprises about 210 amino acids and has a molecular mass of about 21 kilodaltons, depending on the species and subtype.

The amino acid sequence and other physical and chemical information for histone H1 have been described (Isenberg, 1979, Annu. Rev. Biochem. 48:159–191).

The present invention also provides for analogs of histone H1. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups: glycine, alanine; valine, isoleucine, leucine; aspartic acid, glutamic acid; asparagine, glutamine; serine, threonine; lysine, arginine; phenylalanine, tyrosine.

Modifications which do not normally alter primary sequence include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogues of such polypeptides include those containing residues other than naturally occurring L-amino acids, e.g., D-amino acids or non-naturally occurring synthetic amino acids. The peptides of the invention are not limited to products of any of the specific exemplary processes listed herein.

H1 is a native protein in humans and other eukaryotes. Histone H1 is known to be associated with DNA superstructure. Most of the antibiotics that are currently used in humans and animals are or are derived from substances produced by fungi, and thus are foreign substances with respect to humans. Some of the advantages of using histone H1, relative to other antibiotics, include the fact that histone H1 is tissue compatible, in that histone H1 exhibits extremely low immunogenicity. Without being bound by any particular theory, it is believed that histone H1 exhibits low immunogenicity because histone H1 is recognized as a "self" protein by the immune systems of humans and animals. Furthermore, the high degree of sequence identity and relatedness among the histone H1 proteins of various eukaryotes increases the probability that a histone H1 protein obtained from an animal will be recognized as a "self" protein when administered to another animal.

Where the term "histone H1" is used in the present disclosure, the term encompasses any subtype of histone H1 protein expressed in any eukaryote. Preferably the histone H1 is human histone H1, subtype zero, herein designated "histone H1". The compositions, kits, and methods of the invention nonetheless encompass the use of any eukaryotic histone H1.

Histone H1 can be extracted from many tissues of multicellular eukaryotes, and can be isolated to a purity of greater than 99% by weight using standard biochemical procedures such as exclusion/affinity chromatography and/or HPLC, as described (see, e.g. Pehrson et al., 1981, Biochemistry 20:2298–2301). Histone H1 may be prepared from calf thymus, for example, by extraction, as described in U.S. Pat. No. 5,182,257. Histone H1 may also be expressed using a recombinant expression system, such as an expression system which uses $E.\ coli$ or a yeast (Linder et al., 1994, Mol. Cell. Biol. 4:2822–2835; Gerchman et al., 1994, Prot. Express. Purif. 5:242–251). The histone H1 protein used in the compositions, kits, and methods of the invention is preferably in the form of substantially purified histone H1 protein.

As used herein, a "substantially purified" histone H1 protein is one which has been separated from components which naturally accompany it. Typically, histone H1 is substantially pure when at least about 50%, more preferably at least about 70% to 80%, even more preferably at least 90%, and most preferably at least 99% of the total material (as assessed either by wet or dry weight, or by molar fraction) in a sample is histone H1. Purity can be measured by any appropriate method such as, in the case of polypeptides, by column chromatography, gel electrophoresis, or HPLC analysis. Preferably, substantially purified histone H1 protein is separated from more than 90% by weight, and more preferably more than 99% by weight, of the proteins which normally accompany it in a cell.

The present invention includes the discovery that histone H1 exhibits potent antibiotic activity with respect to numerous bacterial strains including, but not limited to, strains which are pathogenic in humans and strains which exhibit resistance to known antibiotics such as penicillin, streptomycin, erythromycin, and vancomycin. Even relatively impure (i.e. 70–80% by weight histone H1) preparations of this protein exhibit the antibiotic effect. The experiments described herein were performed using highly purified (purity>99% by weight, as confirmed by HPLC) histone H1 or highly purified recombinant histone H1 expressed in $E.\ coli$). One skilled in the art will appreciate that the antibiotic effect described herein is attributed to histone H1.

The eukaryotic histone H1 protein useful in the compositions, kits, and methods of the invention may be a chemically modified histone H1. Histone H1 may also be modified to increase serum half-life time or to reduce potential antigenicity. By way of example, the protein may be a polyethylene glycol-derivated eukaryotic histone H1 protein. By way of example, histone H1 can be covalently Icomplexed with polyethylene glycol using known methods. These methods are colloquially referred to in the art as "PEGylation", In addition, up to about twenty amino acid residues may be removed from either or both of the amino- or carboxy-terminal ends of histone H1 protein without significantly affecting the antibiotic activity exhibited by the protein. Modifications such as these have been described in the art (e.g., Isenberg et al., supra).

As used herein, a "chemically modified" histone H1 protein is one which has been treated such that it comprises at least one chemical substituent which reduces the antigenicity or immunogenicity of the protein when it is administered to the bloodstream of a human patient, relative to the naturally-occurring form of the protein. An example of an antigenicity-reducing treatment of a histone H1 protein is the covalent attachment of polyethylene glycol to the histone H1 protein.

Monoclonal antibodies which bind specifically to histone H1 are available to the public, and can be used to monitor the concentration of histone H1 in serum and other tissues or fluids. Such antibodies are commercially available, e.g., from Biogenex, San Ramon, Calif.

The invention also includes an antimicrobial pharmaceutical composition, as described herein, comprising a substantially purified eukaryotic histone H1 protein and a pharmaceutically acceptable carrier. The composition is preferably one which is suitable for injection or infusion into an animal tissue such as blood or one which is suitable for topical application to an animal, as with a composition in the form of a wound dressing. Such a wound dressing may, for example, be selected from the group consisting of a cream, a gel, an absorbent material, and a physiologically degradable material.

Antibacterial activity has been described for arginine-rich histones, but it was reported that lysine-rich histones, such as histone H1, do not exhibit antibiotic activity (Hirsch, 1958, J. Exp. Med. 108:925–944). The antimicrobial pharmaceutical composition of the invention may further comprise a supplemental antibiotic, such as one selected from the group consisting of histones H2A, H2B, H3, H4, and H5. Alternately, the antimicrobial pharmaceutical composition of the invention may further comprise a supplemental antibiotic such as one selected from the group consisting of bacitracin, polymyxin, neomycin, chloramphenicol, chlortetracycline, ciprofloxacin, penicillin, streptomycin, vancomycin, tobramycin, erythromycin, gentamicin, gramicidin, oxytetracycline, norfloxacin, and salts and esters of these antibiotics.

The invention encompasses the preparation and use of pharmaceutical compositions comprising a eukaryotic histone H1 protein as an active ingredient. Such a pharmaceutical composition may consist of the histone H1 protein alone, in a form suitable for administration to a subject. Alternately, the pharmaceutical composition may comprise the histone H1 protein and one or more pharmaceutically acceptable carriers, one or more additional ingredients, or some combination of these. Administration of one of these pharmaceutical compositions to a subject is useful for killing or inhibiting the growth of a microorganism in the subject, as described elsewhere in the present disclosure. The histone H1 protein may be present in the pharmaceutical composition in the form of a physiologically acceptable ester or salt, such as in combination with a physiologically acceptable cation or anion, as is well known in the art.

The invention further encompasses use of a nucleic acid vector comprising a nucleic acid encoding histone H1. The nucleic acid vector may also comprise known promoter, repressor, operator, or other regulatory sequences whereby expression of histone H1 may be controlled upon delivery of the nucleic acid vector to a patient. The invention also encompasses cells which comprise a nucleic acid vector encoding histone H1 and which express histone H1 from that vector.

As used herein, the term "pharmaceutically acceptable carrier" means a chemical composition with which the histone H1 protein may be combined and which, following the combination, can be used to administer the histone H1 protein to a subject.

As used herein, the term "physiologically acceptable" ester or salt means an ester or salt form of the histone H1 protein which is compatible with any other ingredients of the pharmaceutical composition and which not deleterious to the subject to which the composition is to be administered.

The formulations of the pharmaceutical compositions described herein may be prepared by any method known or hereafter developed in the art of pharmacology. In general, such preparatory methods include the step of bringing the histone H1 protein into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys, fish including farm-raised fish and aquarium fish, and crustaceans such as farm-raised shellfish.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the histone H1 protein, and immunologically-based formulations.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the histone H1 protein. The amount of the histone H1 protein is generally equal to the dosage of the histone H1 protein which would be administered to a subject or a convenient fraction of such a dosage such as, for example, one-half or one-third of such a dosage.

The relative amounts of the histone H1 protein, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) histone H1 protein. A unit dose of a pharmaceutical composition of the invention will generally comprise from about 0.1 milligram to about 100 milligrams of the histone H1 protein, and preferably comprises from about 1 milligram to about 10 milligrams of the histone H1 protein.

In addition to the histone H1 protein, a pharmaceutical composition of the invention may further comprise one or more additional pharmaceutically active agents. Particularly contemplated additional agents include antibiotics other than histone H1. Such antibiotics include, but are not limited to, histones H2A, H2B, H3, H4, and H5, bacitracin, polymyxin, neomycin, chloramphenicol, chlortetracycline, ciprofloxacin, penicillin, streptomycin, vancomycin, tobramycin, erythromycin, gentamicin, gramicidin, oxytetracycline, norfloxacin, and salts and esters of these antibiotics.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the histone H1 protein. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the histone H1 protein may, for example, be made by compressing or molding the histone H1 protein, optionally with one or more additional ingredients. Compressed tablets may be prepared by compressing, in a suitable device, the histone H1 protein in a free-flowing form such as a powder or granular preparation, optionally mixed with one or more of a binder, a lubricant, an excipient, a surface active agent, and a dispersing agent. Molded tablets may be made by molding, in a suitable device, a mixture of the histone H1 protein, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pregelatinized maize starch, polyvinylpyrrolidone, and hydroxypropyl methylcellulose. Known lubricating agents include, but are not limited to, magnesium stearate, stearic acid, silica, and talc.

Tablets may be uncoated or they may be coated using known methods to achieve delayed disintegration in the gastrointestinal tract of a subject, thereby providing sustained release and absorption of the histone H1 protein. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the histone H1 protein may be made using a physiologically degradable composition, such as gelatin. Such hard capsules comprise the histone H1 protein, and may further comprise additional ingredients including, for example, an inert solid diluent such as calcium carbonate, calcium phosphate, or kaolin.

Soft gelatin capsules comprising the histone H1 protein may be made using a physiologically degradable composition, such as gelatin. Such hard capsules comprise the histone H1 protein, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the histone H1 protein in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the histone H1 protein in aqueous or oily solvents may be prepared in substantially the same manner as liquid suspensions, the primary difference being that the histone H1 protein is dissolved, rather than suspended in the solvent. Liquid solutions of the pharmaceutical composition of the invention may comprise each of the components described with regard to liquid suspensions, it being understood that suspending agents will not necessarily aid dissolution of the histone H1 protein in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the histone H1 protein with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the histone H1 protein with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the histone H1 protein with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intravenous, intraarterial, intramuscular, or intrasternal injection and intravenous, intraarterial, or kidney dialytic infusion techniques.

Formulations of a pharmaceutical composition suitable for parenteral administration comprise the histone H1 protein combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the histone H1 protein is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the histone H1 protein, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the histone H1 protein in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

The pharmaceutical compositions may be prepared, packaged, or sold in a form suitable for topical administration. Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) histone H1 protein, although the concentration of the histone H1 protein may be as high as the solubility limit of the histone H1 protein in the solvent. Formulations for topical administration may further comprise one or more of the additional ingredients described herein. Formulations for topical administration include, but are not limited to, those intended for external (i.e. dermal) use, those intended for transdermal delivery of the histone H1 protein, and those intended for transmucosal delivery of the histone H1 protein.

A pharmaceutical composition of the invention may be prepared, packaged, or sold in a formulation suitable for pulmonary administration via the buccal cavity. Such a formulation may comprise dry particles which comprise the histone H1 protein and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the histone H1 protein dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the histone H1 protein may constitute 0.1 to 20% (w/w) of the composition. The propellant may further comprise additional ingredients such as a liquid non-ionic or solid anionic surfactant or a solid diluent (preferably having a particle size of the same order as particles comprising the histone H1 protein).

Pharmaceutical compositions of the invention formulated for pulmonary delivery may also provide the histone H1 protein in the form of droplets of a solution or suspension. Such formulations may be prepared, packaged, or sold as aqueous or dilute alcoholic solutions or suspensions, optionally sterile, comprising the histone H1 protein, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the histone H1 protein and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the histone H1 protein, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) histone H1 protein, the balance comprising an orally dissolvable or degradable composition and, optionally, one or more of the additional ingredients described herein. Alternately, formulations suitable for buccal administration may comprise a powder or an aerosolized or atomized solution or suspension comprising the histone H1 protein. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/v) solution or suspension of the histone H1 protein in an aqueous or oily liquid carrier. Such drops may further comprise buffering agents, salts, or one or more other of the additional ingredients described herein. Other ophthalmically-administrable formulations which are useful include those which comprise the histone H1 protein in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

A pharmaceutical composition of the invention may be administered to deliver a dose of between 1 ng/kg/day and 100 mg/kg/day, and preferably to deliver a dose of between 0.1 mg/kg/day and 10 mg/kg/day to a subject.

It is understood that the ordinarily skilled physician or veterinarian will readily determine and prescribe an effective amount of the compound to kill or inhibit the growth of a microorganism in the subject. In so proceeding, the physician or veterinarian may, for example, prescribe a relatively low dose at first, subsequently increasing the dose until an appropriate response is obtained. It is further understood, however, that the specific dose level for any particular subject will depend upon a variety of factors including the activity of the specific compound employed, the age, body weight, general health, gender, and diet of the subject, the time of administration, the route of administration, the rate of excretion, any drug combination, and the severity of the microorganism infection or parasitism being treated.

Inducing Death of a Microorganism Using Histone H1

Histone H1 exhibits broad cytotoxic and cytostatic effects, the effects being dependent upon the target cell type and the concentration of the histone. The concentration of histone H1 that is useful for cytotoxicity or cytostasis of a particular cell type can be determined by the skilled artisan without undue experimentation. By way of example, cytotoxic and cytostatic concentrations of histone H1 may be determined by culturing the cells in the presence and in the absence of a variety of selected concentrations of histone H1 in a suitable medium. By observing the effect of histone H1 concentration on cell number, cytotoxic and cytostatic concentrations will be apparent to the skilled artisan.

Because histone H1 exhibits broad cytotoxic and cytostatic effects, it may be used to kill or arrest growth of microorganisms which are not susceptible to other antibiotic agents. By way of example, antibiotic-resistant bacteria are a problem of increasing magnitude in the field of human health. Ability of a human pathogen to survive administration of one or more antibiotics to a human patient infected with the pathogen can increase the length or severity of the infection. Human pathogens resistant to a variety of known antibiotic agents have been isolated. As described herein, at least certain of these antibiotic-resistant pathogens are susceptible to the antibiotic effect of histone H1. For example, as described herein, penicillin-resistant *Escherichia coli* are killed in the presence of histone H1 at approximately the same concentration of the histone at which wild type *E. coli* are killed. Furthermore, histone H1 has greater antibiotic activity, on a molar basis, than known antibiotic agents such as penicillin and kanamycin.

Included within the invention is a method of inducing death of a microorganism. This method comprises contacting the microorganism with a composition comprising a substantially purified eukaryotic histone H1 protein. Preferably, the microorganism is a human pathogen. By way of example, the cell may also be of a strain of a bacterium which is a human pathogen and which is resistant to known antibiotics such as penicillin or kanamycin. The microorganism may also be a microorganism which is present at a site at which sterility is desired, such as the surface of a surgical instrument or implant, for example. The microorganism may also be a microorganism in a human cell, such as *Chlamydia* cell for example.

According to this method, the microorganism is contacted with an amount of histone H1 protein which is sufficient to kill the microorganism. It is understood that the precise amount of histone H1 protein sufficient to kill a selected microorganism depends upon the identity of the microorganism, the conditions under which the histone H1 protein has been stored, the cell density of the microorganism, and other factors, including physical and chemical characteristics of the environment in which the microorganism is located, which will be apparent to one skilled in the art in view of the present disclosure. It is contemplated that histone H1 protein concentrations in the range from about 0.2 micromolar up to the solubility limit of histone H1 protein will be useful in this cell death-inducing method. As described herein, histone H1 protein concentrations at least as low as about 0.2 micromolar and at least as high as about 4 micromolar are effective to induce the death of at least certain types of bacteria. The skilled artisan may determine a range of cytotoxic histone H1 concentrations for any particular microorganism by following the guidance provided in the present disclosure without significant experimentation.

It is recognized that very high concentrations (i.e. on the order of 10–100 micromolar) of histone H1 may induce death of animal cells. Therefore, in instances in which histone H1 protein is to be used as an antibiotic in an animal such as a human, it is important that the route and dosage of histone H1 protein administered to the animal be selected to maintain the in vivo concentration of histone H1 below a concentration at which histone H1 is cytotoxic toward animal cells. Using nothing other than standard pharmacological testing methods, routes of administration and dosage levels for histone H1 protein may be determined which will minimize histone H1-mediated cytotoxicity in an animal. Given that death of bacterial cells can be induced using relatively low (e.g. 0.2–4 $\mu$M) histone H1 concentrations, as described herein, the skilled artisan will understand that in vivo concentrations of histone H1 may be achieved in an animal which will be effective to induce death of bacterial cells without inducing clinically significant cytotoxicity in an animal infected with the bacterial cells.

Inhibiting Growth of a Microorganism

The invention also includes a method of inhibiting growth of a microorganism. This method comprises contacting the microorganism with a composition comprising a substantially purified eukaryotic histone H1 protein. Use of this method to inhibit growth of human pathogenic bacteria, including multi-drug resistant strains of bacteria, is contemplated. According to this method of the invention, the same composition described for use in the method of inducing cell death described herein, is used in substantially the same way as it is used in that method, it being understood that histone H1 will exhibit cytotoxic activity toward many microorganisms, and cytostatic activity toward others. Nonetheless, inhibiting growth of a microorganism such as a human pathogen reduces the rate at which the severity of the infection increases and enables the infected animal's immune system to mount a stronger reaction to the infection than would be possible in the absence of histone H1-induced growth inhibition of the microorganism.

The invention also includes a method of treating a microbial infection in an animal such as a human. This method comprises administering to the animal an antimicrobial composition comprising a substantially purified eukaryotic histone H1 protein. The composition may be administered to the animal by an oral, rectal, vaginal, parenteral, topical, pulmonary, intranasal, buccal, ophthalmic, or another route of administration. Pharmaceutical compositions suitable for administration by these routes are described herein.

The invention still further includes a method of inhibiting microbial growth at a selected site which may, for example, be a site on or within the body of an animal such as a human, a site on or in a non-living object, or a site at or on which microbial growth is suspected or is known to be present. This method comprises providing an antimicrobial composition comprising a eukaryotic histone H1 protein to the site. In one aspect of this method, the composition is provided to the site by incorporating the composition into the site, such as by synthesizing an object using a material which comprises the composition. By way of example, microbial growth may be inhibited in an injectable pharmaceutical composition by including a eukaryotic histone H1 protein in the composition. Further by way of example, the site may be a site on or within a foodstuff. When the site is on or within the body of the animal, the composition may be provided to the site at the time of or before surgery, so that infection is prevented or inhibited by inhibiting microbial growth at the site.

In another embodiment of this method, the composition is provided to the site by providing the composition to a surface which contacts the site. The surface may be an animal surface, such as the surface of a wound of a wounded animal, or it may be an inanimate surface, such as a food preparation surface or the surface of a surgical implement. Furthermore, the surface may be the surface of a biodegradable implant which comprises the composition and which is implanted within the body of an animal such as a human.

It is known in the art that supplementing animal feed with one or more antibiotics results in improved growth of animals such as cattle and other farm animals which ingest the feed. The invention thus includes a supplemented animal feed comprising an animal feed supplemented with an antimicrobial composition comprising a substantially purified eukaryotic histone H1 protein. The invention also includes a method of improving growth of a non-human animal, the method comprising feeding the animal the histone H1-supplemented animal feed.

The invention further includes a method of vaccinating an animal against a microorganism. This method comprises administering to the animal a composition comprising an attenuated or killed form of the microorganism and a substantially purified eukaryotic histone H1 protein. As described in U.S. Pat. No. 5,182,257, histones, including histone H1, exhibit immunostimulatory effects, meaning that the activity of immune system components is increased when a histone is administered to an animal. Because histone H1 also exhibits antimicrobial activity, a vaccine may be made by contacting a microorganism with histone H1 in a mixture in order to kill the microorganism, and then administering the mixture to an animal to immunize the animal with respect to the microorganism. The vaccine prepared in this way contains both the killed microorganism comprising an antigen and an immunostimulatory histone, preferably histone H1. The invention thus includes a method of preparing a vaccine, a vaccine prepared by that method, and a method of immunizing an animal comprising administering a vaccine prepared in the disclosed manner to the animal.

The Kit of the Invention

The invention additionally includes a kit comprising the antimicrobial pharmaceutical composition of the invention and an instructional material selected from the group consisting of an instructional material which describes use of the antimicrobial composition to kill a microorganism and an instructional material which describes use of the antimicrobial composition to arrest the growth of a microorganism. Preferably, the composition is in a unit dosage form.

In one embodiment of the kit of the invention, the kit further comprises a second composition which comprises a histone H1 antidote such as heparin. In another embodiment, the kit further comprises an instructional material which describes administration of the histone H1 antidote to an animal which exhibits an adverse reaction to administration thereto of histone H1.

As used herein, an "instructional material" includes a publication, a recording, a diagram, or any other medium of expression which is used to communicate the usefulness of the pharmaceutical composition of the invention for killing or inhibiting the growth of a microorganism in a subject. The instructional material may also, for example, describe an appropriate dose of the pharmaceutical composition of the invention. The instructional material of the kit of the invention may, for example, be affixed to a container which contains a pharmaceutical composition of the invention or be shipped together with a container which contains the pharmaceutical composition. Alternatively, the instructional material may be shipped separately from the container with the intention that the instructional material and the pharmaceutical composition be used cooperatively by the recipient.

The invention also includes a kit comprising a pharmaceutical composition of the invention and a delivery device for delivering the composition to a subject. By way of example, the delivery device may be a squeezable spray bottle, a metered-dose spray bottle, an aerosol spray device, an atomizer, a dry powder delivery device, a self-propelling solvent/powder-dispensing device, a syringe, a needle, a tampon, or a dosage measuring container. The kit may further comprise an instructional material as described herein.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLE 1

Preparation of Purified Bovine Histone

Histones were purified according to Pehrson et al. (1981, Biochemistry 20:2298–2301).

EXAMPLE 2

Preparation of Recombinant Human Histone H1 in *Escherichia coli*

Recombinant human histone H1 may be prepared in *E. coli* as described in Gerchman et al., 1994. Prot. Express. Purif. 5:242–251, supra.

EXAMPLE 3

Preparation of Recombinant Human Histone H1 in Yeast

Recombinant human histone H1 may be prepared in yeast as described in Linder et al. 1994. Mol. Cell. Biol. 4-2822-2835.

EXAMPLE 4

Concentration Dependency of the Cytotoxicity of Histone H1

Purified bovine histone H1 was prepared as described herein in Example 1. Cells of *E. coli* strain AB1157 (obtained from ATCC) were grown in NYET medium (4 grams per liter nutrient broth, 7.5 grams per liter yeast extract, and 4 grams per lither tryptone) at 37° C. *E. coli* cells in approximately the exponential growth phase were incubated in Sorensen buffer (41 mM Na2HPO4, 25.7 mM KH2PO4) for twenty minutes in the presence of a selected concentration of histone H1. The fractional survival of histone H1-contacted cells, relative to cells which were not contacted with histone H1 was determined by counting colonies using an automated colony counter (3M model 620). About 200 microliters of an H1-containing bacterial suspension was plated into Petri dishes by adding 10 milliliters of 57° C. medium containing 1.5% (w/w) Bacto agar. Histone H1 was heat inactivated and diluted 50-fold by this procedure, with the result that the concentration of H1 was no longer biologically active.

As indicated in FIG. 1 and FIG. 1A, more than 98% of *E. coli* cells were killed following contact of the cells with a suspension having a histone H1 concentration less than 1 micromolar. Significant cytotoxicity was observed at H1 concentrations as low as 0.24 micromolar.

Figure 2:
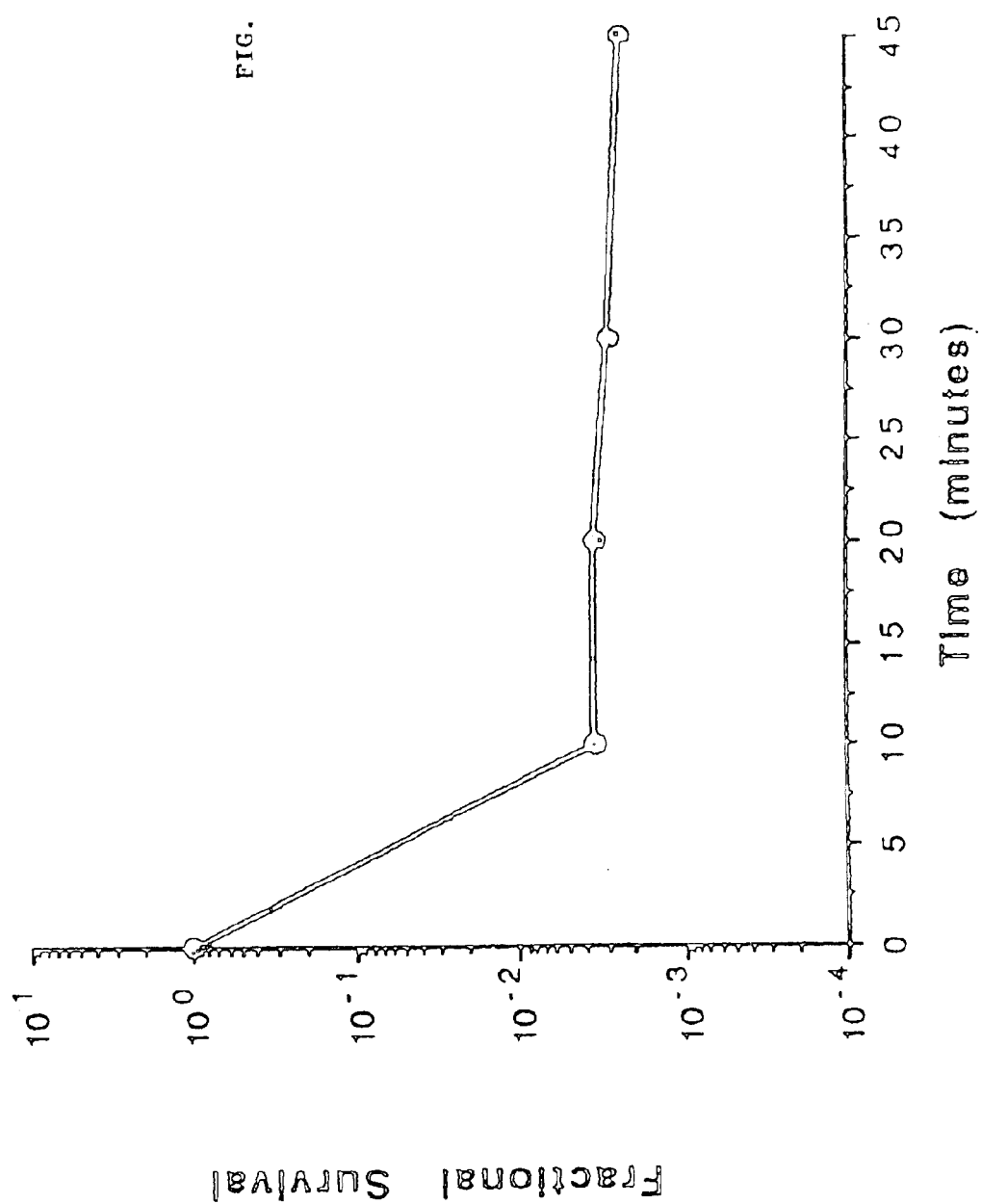
FIG. 2 is a graph which indicates the exposure time dependence of the antibiotic activity exhibited by histone H1 with respect to *E. coli* strain AB1157.

Incubating the cells at 37° C. with a composition comprising 1.9 micromolar H1 for less than ten minutes was sufficient to achieve maximal cytotoxic effect. Longer incubation did not result in higher killing, as indicated in FIG. 2.

The cytotoxic efficacy of histone H1 was compared to the efficacies of equal concentrations of penicillin and kanamycin. *E. coli* strain AB1157 cells were incubated at 37° C. for ten minutes in Sorensen buffer which comprised one of 1.9 micromolar histone H1, 1.9 micromolar penicillin, and 1.9 micromolar kanamycin. Cytotoxicity effected by incubation of the cells in the presence of histone H1 was more than one hundred times greater than cytotoxicity effected by incubation of the cells in the presence of penicillin. Incubation of the cells in the presence of kanamycin resulted in no measurable cytotoxicity.

The experiments presented in this Example demonstrate that histone H1 kills bacteria faster and more efficiently than either penicillin or kanamycin at an equal concentration.

EXAMPLE 5

Temperature Dependency of the Antibiotic Effects of Histone H1

Purified bovine histone H1 was prepared as described herein in Example 1. Cells of *E. coli* strain AB1157 were incubated in Sorensen buffer at a selected temperature for a selected period in the presence of a 1.9 micromolar histone H1 The fractional survival of histone H1-contacted cells, relative to cells not contacted with histone H1 was determined as described herein in Example 4. It was observed that the bactericidal effect of histone H1 was significantly greater at 37° C. than at either 4° C. or 30° C. Normal human body temperature is about 37° C.

The results of the experiments presented in this Example indicate that histone H1 exhibits greater bacteriocidal effect at normal human body temperature than it does at lower temperatures. Thus, it is necessary to use a higher concentration of histone H1 in situations in which the temperature is lower than normal human body temperature in order to achieve an equivalent bacteriocidal effect. Thus, a topical antibiotic preparation for antiseptic use on human skin wounds, for example, may comprise a higher concentration of histone H1 than would a preparation intended for intravenous injection into a human.

EXAMPLE 6
Bacteriocidal Effect of Histone H1 Upon Penicillin-Resistant Bacteria

Purified bovine histone H1 was prepared as described herein in Example 1. Cells of *E. coli* strain AB1157 or (separately) cells of a penicillin-resistant *E. coli* strain derived from strain AB1157 were incubated in Sorensen buffer at 37° C. for a selected period in the presence of a 1.9 micromolar histone H1. Cells of *E. coli* strain AB1157 were made penicillin-resistant by culturing them in penicillin-containing growth media over a period of several days. The resulting population was completely resistant to penicillin. The fractional survival of histone H1-contacted cells, relative to cells not contacted with histone was determined as described herein in Example 4.

Figure 3:
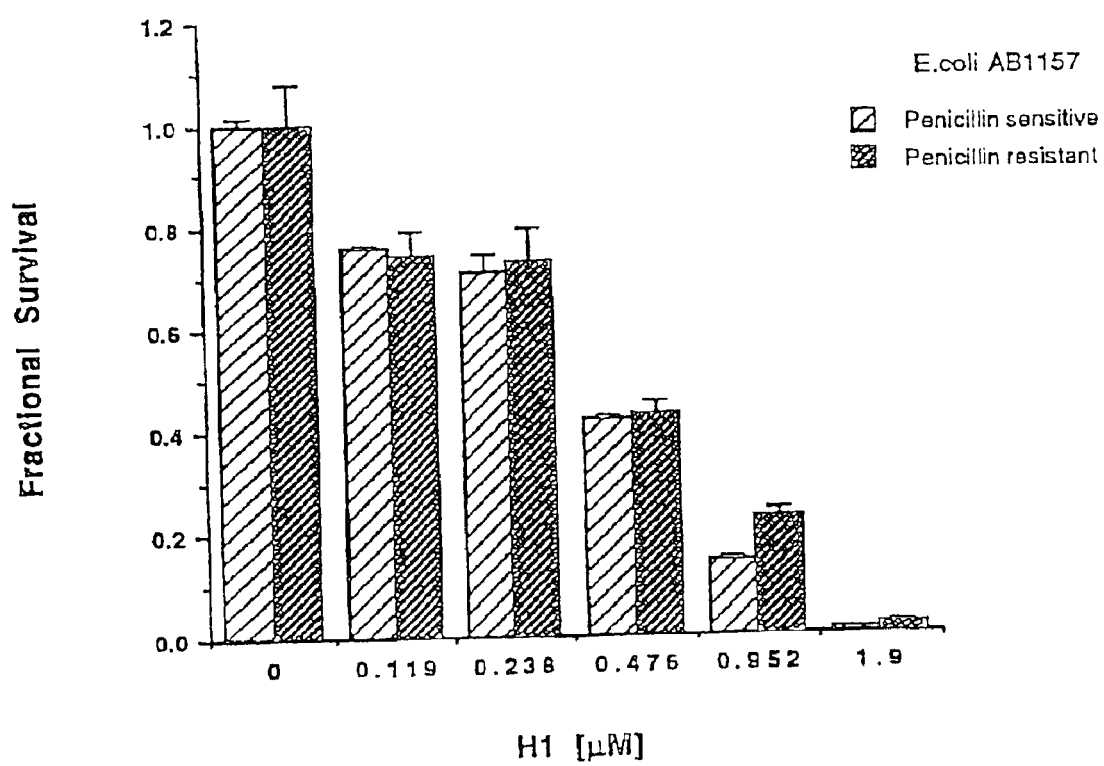
FIG. 3 is a bar graph which compares of the antibiotic activity exhibited by histone H1 of penicillin-sensitive *E. coli* strain AB1157 with the antibiotic activity with respect to a penicillin resistant strain of *E. coli* derived from strain AB1157 as described herein in Example 6 at various concentrations at Histone H1. Survival of penicillin sensitive *E. coli* cells is indicated by the bars having less dense stripes. Survival of penicillin-resistant *E. coli* cells is indicated by the more heavily-striped bars.

As indicated in FIG. 3, histone H1 killed penicillin-resistant cells approximately as efficiently as it killed wild type cells. These results indicate that histone H1 can be used to treat infections involving drug resistant bacteria. The bacteriocidal effects of histone H1 were not affected by the bacterial mechanism(s) which conferred penicillin resistance to the bacteria.

EXAMPLE 7
Tertiary Structure Dependence of the Antibiotic Activity of Histone H1

Purified bovine histone H1 was prepared as described herein in Example 1. Proteolytically digested histone H1 was prepared by incubating purified histone H1 in Sorensen buffer containing 0.05% (w/v) trypsin for thirty minutes at room temperature (i.e. about 20° C.). Cells of *E. coli* strain AB1157 were incubated in Sorensen buffer at 37° C. for twenty minutes in the presence of either 1.9 micromolar histone H1 or 1.9 micromolar trypsinized histone H1 The fractional survival of histone H1-contacted cells, relative to cells not contacted with histone H1 was determined as described herein in Example 4.

Trypsinized histone H1 did not exhibit antibiotic activity, while non-trypsinized histone H1 did. Trypsin alone had no effect on the survival of the bacteria. These results indicate that the antibiotic effect of histone H1 is attributable to binding of the histone to a particular biological molecule of target cells, and that the antibiotic effect of histone H1 is not attributable merely to the physical characteristics of the components of the histone (e.g. the mere presence of or the basic nature of the amino acid side chains of histone H1). These results furthermore suggest that the antibiotic effect of histone H1 is attributable to a specific protein—protein interaction between the histone and a target cell protein.

EXAMPLE 8
Thermal Stability of Histone H1

Purified bovine histone H1 was prepared as described herein in Example 1. In a first experiment, purified histone H1 was stored at −80° C. for more than thirty-six months. The antibiotic activity of histone H1 was not significantly decreased by this storage method.

In a second experiment, aliquots of purified histone H1 were separately stored at −80° C., at 4° C., and at 37° C. for twenty hours. Cells of *E. coli* strain AB1157 were thereafter incubated in Sorensen buffer at 37° C. for ten minutes in the presence of 40 micrograms per milliliter histone H1 obtained from one of the three aliquots. The fractional survival of histone H1-contacted cells, relative to cells not contacted with histone H1 was determined as described herein in Example 4. The fractional survival of cells incubated with histone H1 stored at −80° C. was about 0.1%. The fractional survival of cells incubated with histone H1 stored at 4° C. was about 1%. The fractional survival of cells incubated with histone H1 stored at 37° C. was about 6%.

The results of the experiments described in this Example indicate that the antibiotic activity of histone H1 may be preserved by storing the enzyme at or below −20° C., and preferably at or below −80° C. Histone H1 should be used within six hours after thawing. In addition, these results indicate that histone H1 may be stored at −80° C. for at least thirty-six months without activity loss, and preferably is stored no more than about twenty-four months before use.

EXAMPLE 9
Spectrum of Antibiotic Activity of Histone H1

Purified bovine histone H1 was prepared as described herein in Example 1. Cultures of various test bacteria were made in appropriately selected media, and the cells were incubated until the cultures were estimated, using standard procedures, to be exhibiting early log phase growth. Histone H1 suspended in Sorensen buffer was added to aliquots of individual bacterial cultures to achieve a final concentration of either 1.9 micromolar or 3.8 micromolar. No histone H1 was added to individual control culture aliquots. The aliquots were thereafter incubated at 37° C. for either ten minutes or forty-five minutes, and the aliquots were plated on appropriate solid or semisolid media. The following day, colony number was enumerated in the plated aliquots, and the percent reduction in colony formation, as indicated in Table 1, was determined by comparing colonies formed in plated histone H1-treated aliquots with colonies formed in plated control aliquots.

TABLE 1

| Organism | Percent Reduction in Colony Formation | | | |
|---|---|---|---|---|
| Incubation time | 10 minutes | | 45 minutes | |
| [Histone H1]$_{micromolar}$ | 1.9 | 3.8 | 1.9 | 3.8 |
| *Escherichia coli* strain AB1157 | 99.6 | 99.9 | 99.7 | 100 |
| *Pseudomonas aeruginosa* | 99.6 | 100 | 100 | 100 |
| *Salmonella enteritidis* | >99 | — | — | — |
| *Bacillus subtilis* | 97.4 | — | — | — |
| *Bacillus megaterium* | 93.3 | 91.2 | 92.9 | 99.3 |
| *Bacillus cereus* | 11.8 | 50.7 | 42.5 | 77.4 |
| *Serratia marcescens* | 14.0 | — | — | — |
| *Staphylococcus aureus* | 0.0 | 0.0 | 0.0 | 0.0 |
| *Enterococcus faecalis* | 0.0 | 0.0 | 0.0 | 0.0 |
| *Proteus mirabilis* | 0.0 | — | — | — |

The data in Table 1 indicate that histone H1 exhibited antibiotic activity with respect to *Escherichia coli* strain AB 1157, *Pseudomonas aeruginosa, Bacillus subtilis, Bacillus megaterium, Bacillus cereus*, and *Serratia marcescens*.

Figure 9:
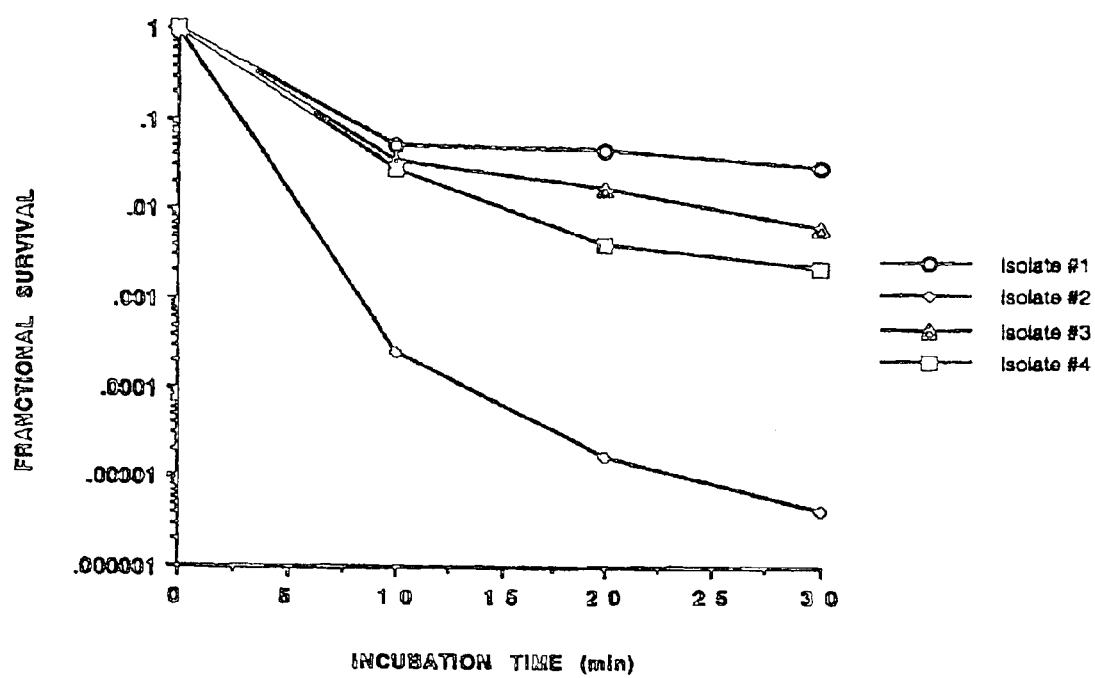
FIG. 9 is a graph which indicates the exposure time dependence of the antibiotic activity exhibited by histone H1 with respect to various *E. coli* strains derived from urinary tract infections.

As indicated by FIG. 9, histone H1 exhibited antibiotic activity with respect to various strains of *E. coli* isolated from urinary tract infections. After thirty minutes all strains displayed less than 3% survival.

It is anticipated that histone H1 will exhibit antibiotic activity with respect to at least the bacteria listed in Table 2.

TABLE 2

Histone H1-Susceptible Bacteria

*Escherichia coli, Klebsiella pneumoniae, Shigella* species, *Bacillus cereus, Pseudomonas aeruginosa, Proteus morgani, Staphylococcus albus, Salmonella typhimurium, Bacillus megaterium, Serratia marcescens, Bacillus subtilis, Salmonella enteritidis*

EXAMPLE 10

Serum Independence of the Antibiotic Activity of Histone H1

Purified bovine histone H1 was prepared as described herein in Example 1. Cells of *E. coli* strain AB1157 were incubated in Sorensen buffer at a selected temperature for a selected period in the presence of a selected concentration histone H1. In selected assays, the medium also contained between 0 and about 10% (v/v) human or bovine serum. The fractional survival of histone H1-contacted cells, relative to cells not contacted with histone H1 was determined as described herein in Example 4.

The antibiotic activity of H1 was determined to be independent of serum concentrations at concentrations at least as high as 10% (v/v) serum, using either human AB serum or fetal calf serum. Based on these observations, one skilled in the art would understand that histone H1 will exhibit its antibiotic activity even in serum-containing environments, such as the human bloodstream.

EXAMPLE 11

Inhibitors of the Antibiotic Activity of Histone H1

Purified bovine histone H1 was prepared as described herein in Example 1. Cells of *E. coli* strain AB1157 were incubated in Sorensen buffer at a 37° C. for ten minutes in the presence of 4 micrograms per milliliter histone H1. In selected assays, the incubation medium also contained a selected concentration of heparin, in the range from 0 to about 250 units per milliliter. The fractional survival of histone H1-contacted cells, relative to cells not contacted with histone H1 was determined as described herein in Example 4.

Figure 4:
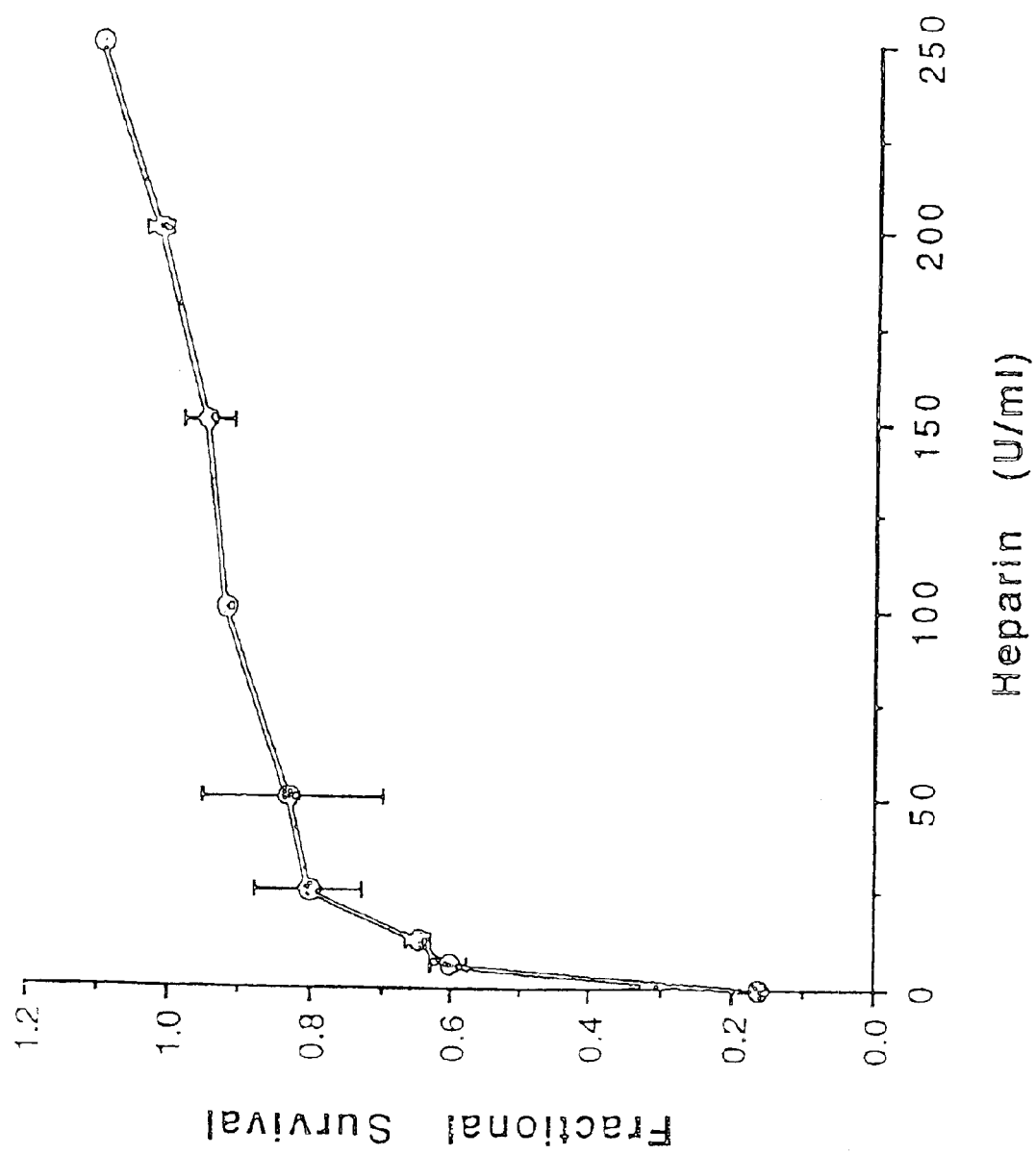
FIG. 4 is a graph which indicates the dependence of the antibiotic activity exhibited by histone H1 with respect to *E. coli* strain AB1157 upon the concentration of heparin in the histone-cell contacting medium.

As indicated in FIG. 4, heparin reduced the antibiotic activity of histone H1 at concentrations as low as 6.2 units per milliliter. At concentrations greater than about 150 units per milliliter heparin, histone H1 exhibited essentially no antibiotic activity. These results indicate that the antibiotic activity of histone H1 can be arrested by addition of heparin to the histone H1-containing medium. These results further suggest that any adverse cytotoxic activity that histone H1 may potentially exhibit when administered to a subject such as a human can be halted by administration of heparin to the histone H1-containing site of the subject. By way of example, hemolytic activity observed in a histone H1-sensitive human patient following intravenous administration of the histone H1 may be inhibited or eliminated by intravenous administration of heparin to the patient.

EXAMPLE 12

Development of Bacterial Resistance to the Antibiotic Activity of Histone H1

Purified bovine histone H1 is prepared as described herein in Example 1. Cells of *E. coli* strain AB1157 are incubated in aliquots of Sorensen buffer containing various set concentrations of histone H1. The aliquot having the highest histone H1 concentration in which cells proliferate (as indicated, for example, by turbidity of the buffer) is used to seed cultures having even higher histone H1 concentrations. This process is repeated until cells are isolated which grow at a concentration of histone H1 that is normally toxic to *E. coli* cells.

As described herein in Example 6, histone H1 kills bacteria relatively rapidly (i.e. within about ten minutes). It is known that by rapidly killing bacteria using an agent, selection pressure for development of bacterial resistance to the agent is reduced (Desnottes, 1998, The Scientist 12:6). In view of these data the skilled artisan will understand that the development of histone H1-resistant bacteria should be no more, and likely less, likely than development of bacteria resistant to known antibiotics.

EXAMPLE 13

Binding of Histone H1 to Bacteria

Figure 5:
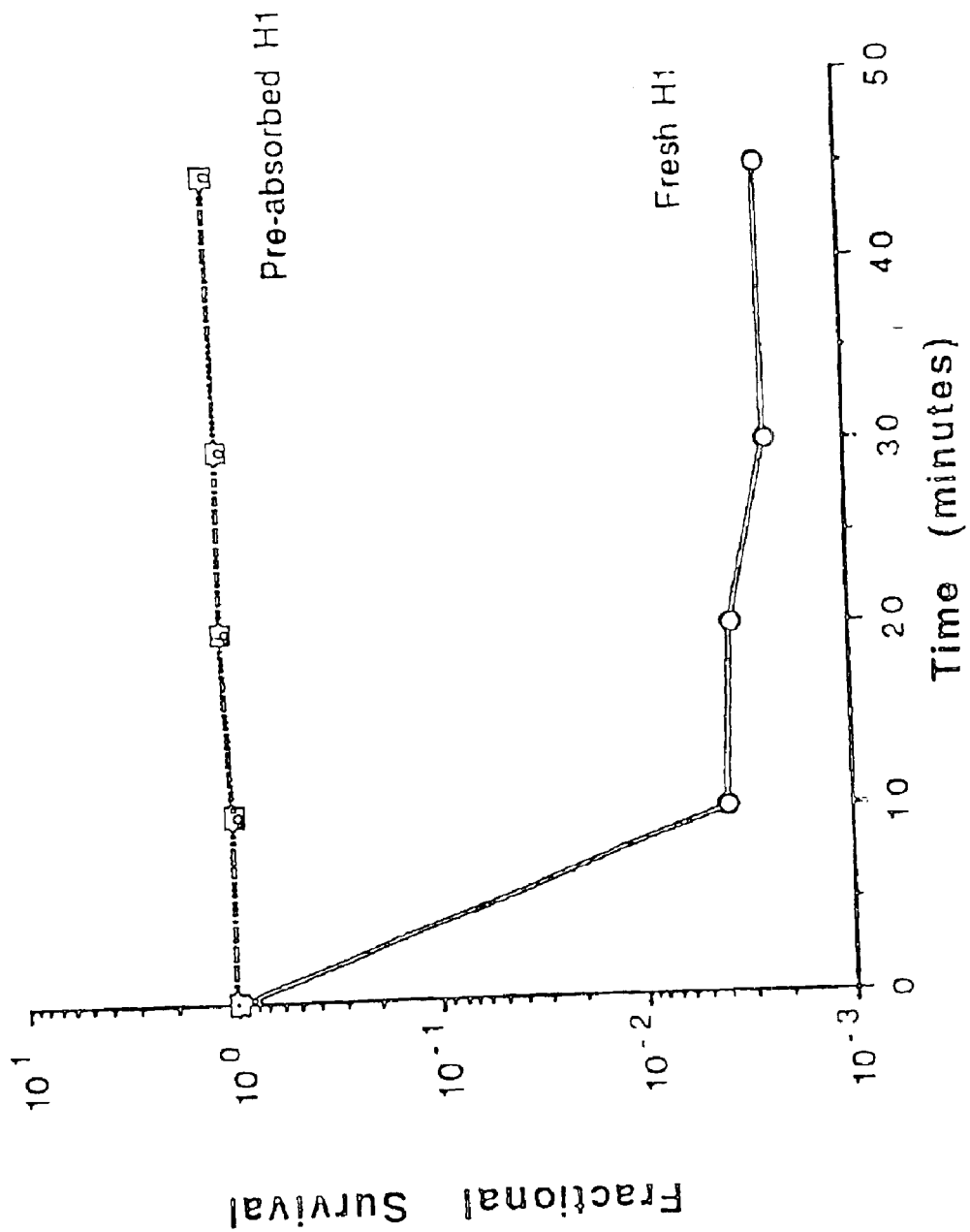
FIG. 5 is a graph which compares the antibiotic activity exhibited by a preparation of histone H1 with respect to *E. coli* strain AB1157 and the antibiotic activity exhibited by an analogous preparation of histone H1 which had been pre-contacted with *E. coli* cells. The preparation of non-pre-absorbed histone H1 is represented on the graph by a line marked with circular points. Pre-contacted histone H1 is represented on the graph by a line marked with square points.
Figure 6:
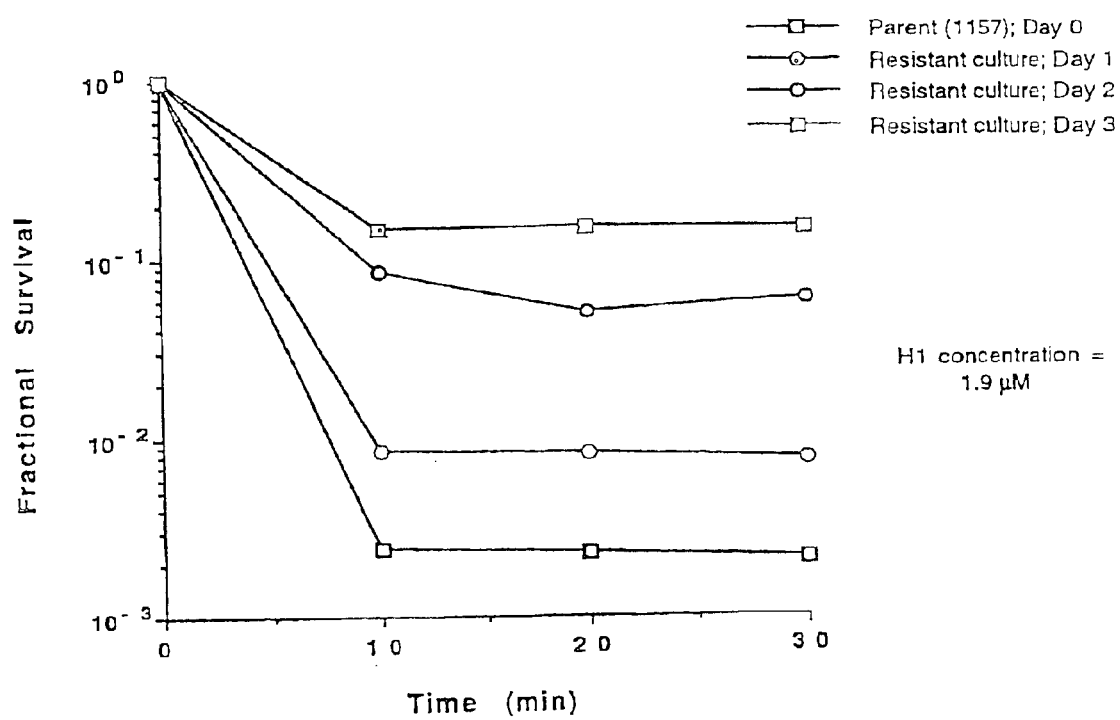
FIG. 6 is a graph which indicates that *E. coli* cells can develop resistance to the antibiotic activity of Histone H1.

Purified bovine histone H1 was prepared as described herein in Example 1. An aliquot of cells of *E. coli* strain AB1157 was incubated with histone H1 as described herein in Example 4. After forty-five minutes of incubation, cells were removed by centrifugation and decanting. The decanted medium was inoculated with fresh *E. coli* cells, and the fractional survival of these cells was determined as described in Example 4, compared to a sample of cells incubated with freshly prepared histone H1. The results of this experiment are presented in FIG. 5.

The H1-containing incubation medium was apparently cleared of antibiotically active H1 molecules by incubating the medium with *E. coli* cells. The results of the experiments described in this Example indicate that histone H1 binds specifically to bacteria in a non-reversible manner. These results suggest that the antibiotic activity of H1 is a target-specific, selective mechanism that depends on the presence of an H1-ligand on the surface of susceptible bacteria.

EXAMPLE 14

Effect of Histone H1 on Bacterial Membrane Integrity

Purified bovine histone H1 was prepared as described herein in Example 1. Cells of *E. coli* strain AB1157 were incubated in Sorensen buffer in the presence of various concentrations of histone H1 at 37° C. Membrane damage of *E. coli* cells was determined at various time intervals, using the dye Sytox Green and a flow cytometer as described (Roth et al., 1997, Appl. Env. Microbiol. 63:2421–2431).

Figure 7:
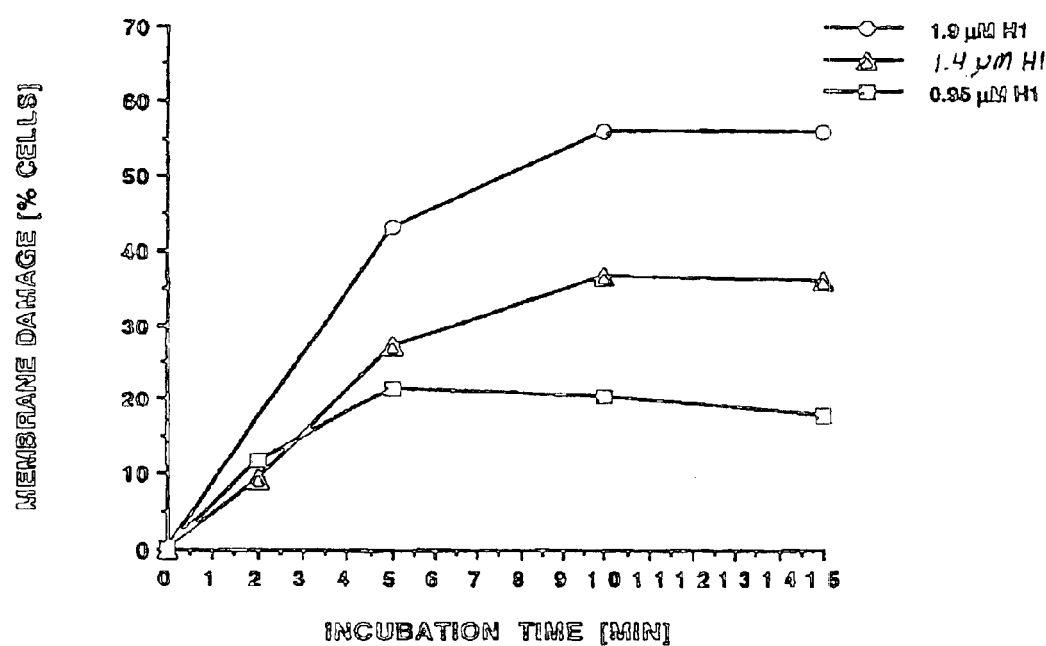
FIG. 7 is a graph which indicates that the disruption of membrane integrity is responsible for the bactericidal effects of histone H1. The graph compares the percentage of membrane damaged cells with the incubation times of various concentrations of histone H1. Filled circular points mark a line representing 1.9 $\mu$M histone H1, white triangular points mark a line representing 0.4 $\mu$M histone H1, and filled square points mark a line representing 0.95 $\mu$M histone H1.

As indicated by the data presented in FIG. 7, the fraction of the cells which exhibited membrane damage was dependent on the concentration of histone H1 present in the medium.

The results of the experiments presented in this Example indicate that the disruption of membrane integrity is associated with the antibiotic activity of H1, which suggests that membrane-disrupting effects of H1 may be responsible for the bactericidal effects of histone H1.

EXAMPLE 15

Bactericide-Enhancing Effects of Histone H1

Purified bovine histone H1 was prepared as described herein in Example 1. Cells of *E. coli* strain AB1157 were incubated in Sorensen buffer at 37° C. for ten minutes with histone H1, lysozyme, and a combination of histone H1 and lysozyme. The fractional survival of these cells was determined as described in Example 4.

Figure 8:
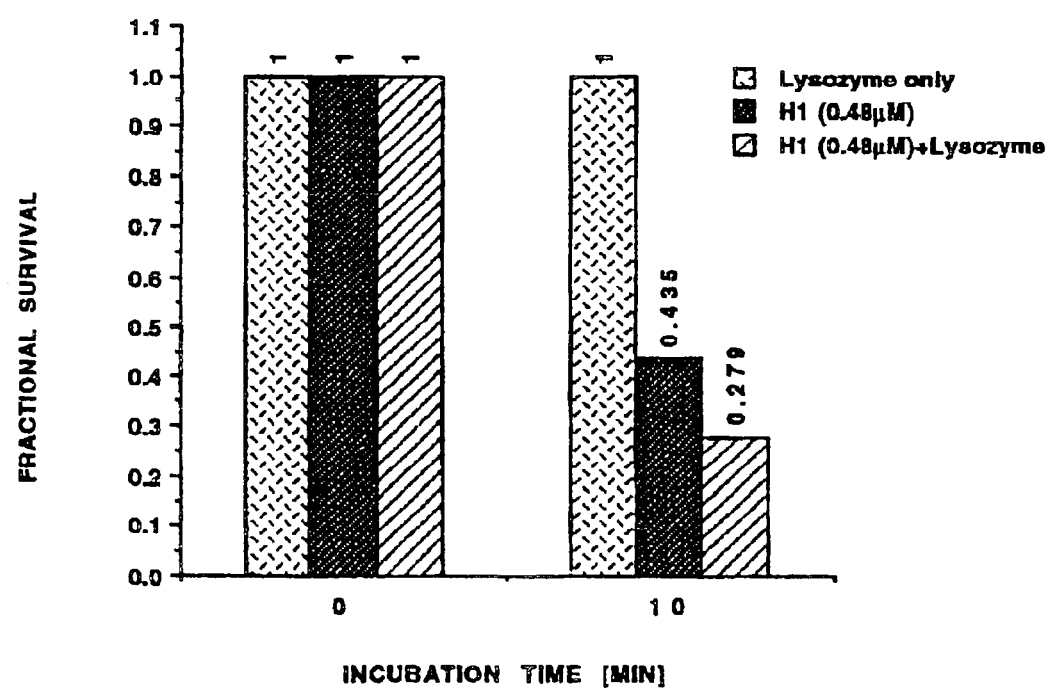
FIG. 8 is a graph which compares the antibiotic activity exhibited by histone H1, lysozyme, and a preparation of histone H1 co-incubated with lysozyme. Antibiotic preparation of lysozyme only is represented by the bar with cross-hatches. Preparation of 0.48 $\mu$M of histone is indicated by the bar having heavily striped bars. The preparation of 0.48 $\mu$M of histone H1 with lysozyme is indicated by the bar having less dense stripes.

As indicated in FIG. 8, lysozyme exhibited essentially no antibiotic activity when incubated without histone H1. Co-incubation with histone H1 increased the antibiotic activity attributable to lysozyme. These results suggest that histone H1 enhances the bactericidal effect of compounds with which it is co-incubated or co-administered.

Resistance Against Histone H1

The antibiotics of the prior art inhibit growth of microorganisms or cause death of microorganisms by directly interfering with some essential biochemical pathway of bacterial metabolism. Most known antibiotics interfere with high specificity with individual steps of biochemical pathways, and lead to specific defects, mostly of central metabolism involved in the synthesis of precursor molecules of cellular macromolecules, e.g. peptidoglycan synthesis, synthesis of membrane lipids, amino acid biosynthesis, transcription, translation and DNA replication. The mechanisms of action of a large number of antibiotics have been determined in the prior art to the molecular level. In these studies, the phenomenon of spontaneous resistance has been of great advantage. Thus, it has been often observed, that resistance against an antibiotic is a result of a single mutation in an individual enzyme of a metabolic pathway. In this way, in most cases, it has become possible to indicate tan individual enzyme of a biochemical pathway, that is specifically inhibited by a given antibiotic, and in addition, to indicate which part of the enzyme has to be structurally altered by mutations, in order to confer resistance against the antibiotic.

The antibiotics of the prior art interfere with high specificity with the activity of individual enzymes of bacterial metabolism and therefore, a common cause of resistance is often a structural alteration of the target enzyme, that is specifically inhibited by an antibiotic. Other common mechanisms of bacterial resistance against antibiotics are increased cellular concentrations of the sensitive target enzyme and the decreased uptake or enhanced efflux of the antibiotic from the cell by a number of mechanisms. All of the aforementioned bacterial resistance mechanisms against the antibiotics of the prior art are based on a common principle, namely on the interference with the highly specific interaction of a given antibiotic with its cellular target. Thus, resistance to the antibiotics of the prior art, e.g. by the above-described specific resistance mechanisms, can easily be acquired by bacteria, by interfering in some way with the specific interaction between an antibiotic and its cellular target. As described above, bacteria can acquire a variety of simple but effective resistance mechanisms against the highly specific antibiotics of the prior art by spontaneous mutations in single genes.

The mechanism of antibiotic action of histone H1 is distinct from the mechanisms of action of the antibiotics of the prior art, in that H1 interacts with the bacterial membrane, and changes or disrupts the native membrane structure, thereby causing cellular lysis and death of the bacterium. The antibiotic activity of histone H1 therefore is a result of the capacity of histone H1 to interact with biological membranes and to disrupt their native structure. The ability of histone H1 to interact with and disrupt cellular membranes is not specific for bacterial membranes, but is also observed with eucaryotic and archaeal membranes, and can be used e.g. in the therapy of human tumors. However, as described herein, there is a markedly increased sensitivity of bacterial membranes to histone H1 as compared with eucaryotic membranes, such as the cellular membranes of fungi or human cells. This allows to use histone H1 as an antibiotic within the human body.

Bacteria cannot easily acquire resistance against histone H1, because histone H1 interacts with the bacterial membrane as such, rather than with a single specific cellular protein. Therefore, mutations in single genes cannot lead to bacterial resistance against histone H1. Bacteria would have to change the structure of their membranes considerably, in order to become tolerant against the general membrane-damaging properties of histone H1. Therefore, resistance against histone H1 cannot be acquired by bacteria so rapidly as with the antibiotics of the prior art, and is less likely to occur. Changes in the overall structure of the bacterial membrane that might confer resistance against histone H1 would necessitate a variety of mutations in different genes, whereas resistance against the antibiotics of the prior art often results from single mutations. In addition, changes in the overall structure of the cellular membrane are most likely to interfere with some of the multitude of functions of the bacterial membrane and to be detrimental to the growth or survival of the whole cell.

Resistance against the antibiotic action of histone H1 can be less easily acquired by bacteria than resistance against the antibiotics of the prior art. Therefore histone H1 can be used for the treatment of infections with multi-resistant bacterial strains. Histone H1 can in addition be used in situations where antibiotics should not be used in order to avoid the development of resistant bacterial strains, such as in the breeding of animals, in the production and conservation of food, in personal care products etc.

As disclosed herein, histone H1 can in addition be used in combination with other bactericidal compounds, because of its distinct mechanism of action. With great advantage, histone H1 can be used in combination with bactericidal agents, such as lysozyme, that disrupt the peptidoglycan layer of gram positive bacteria, and make the bacterial membrane accessible to histone H1.

Interaction of Histone H1 with Heparin

As mentioned above, histone H1 has a general capacity to bind to and disrupt the structure of biological membranes. However, as disclosed herein, bacterial cells differ largely from eucaryotic cells, e.g. fungal and human cells, in their sensitivity against histone H1. The toxic concentrations of histone H1 for bacteria are disclosed herein, that are considerably lower than for fungi and are in particular considerably lower than for human cells. Histone H1 can therefore be applied to patients, e.g. for the treatment of bacterial infections, without any risk to the patient. However, for sensitive patients and for difficult situations, the present invention provides for an antidote against histone H1, that can readily be administered to the patient to specifically bind and thus inactivate histone H1.

According to a further embodiment of the invention, heparin is provided as an antidote against histone H1. Heparin is a pharmaceutical compound that has been used for many years in order to prevent blood clotting, e.g. during or after surgery. The use of heparin as an antidote against histone H1 is an inventive new application of heparin. Pharmaceutical compositions, that can be administered to a patient without risk for the above-mentioned inventive new application of heparin can be taken from the prior art. In particular, the save incorporation of heparin into infusates and the non toxic dosages of heparin that can be administered to a patient, are known in the prior art.

Heparin specifically binds to and inactivates histone H1. This is at least in part due to the fact, that heparin is a polyanion and therefore interacts readily with histone H1, that carries multiple positive charges. Therefore, further antidotes of the invention against histone H1 are any soluble polyanions that bind to histone H1 and can be administered to a patient without risk, and in particular any soluble polyanions that can be incorporated into an infusion solution.

According to still another embodiment of the invention, histone H1 can be used as antidote against heparin. Heparin is frequently used during or after surgery to prevent blood clotting. In particular, during heart surgery, patients are injected large quantities of heparin, in order to prevent blood clotting. After surgery, the heparin is routinely removed, in many cases by injections of protamine. Protamine is similar to histone H1, because of its high content of positively charged basic amino acids. Although the physiologic functions of protamine and histone H1 are different, histone H1 can be therapeutically used instead of protamine for the removal of unwanted heparin. Therefore the invention provides histone H1 as antidote against heparin, in particular, but not limited to, for the binding and inactivation of unwanted heparin after surgical treatment, in particular after heart surgery.

Incorporation of Histone H1 into Sterile Materials

In further embodiments of the invention, histone H1 is incorporated into sterile materials. In these embodiments, histone H1 is linked to the surface of sterile articles or is continuously released from sterile articles, such as surgical implants, long-term catheters, band aids or wraps of synthetic polymers for perishable food.

In surgical implantations, such as e.g. hip replacement surgery, there exists a long-term risk of recurrent infections at the implantation site. It has been observed, that bacterial infections at the implantation site can occur up to several years after the successful implantation. It is generally believed, that in these cases bacteria are introduced into the implantation site together with the implant or on the surface of the implant. For unknown reasons, the bacteria remain in an inactive state or remain under the control of the innate immune defense for up to several years. At a later stage, however, the resting bacteria can become activated and begin to proliferate, causing an infection at the implantation site.

In the above-described cases of local infections at implantation sites, pathogenic bacteria are introduced into the implantation site on the surface of an implant that was not properly sterilized, or enter the wound during surgery by contamination from the surrounding. Therefore, an additional bactericidal action at the implantation site is needed, in addition to the sterilization of the implant, in order to avoid the above-described infections. According to an embodiment of the invention, histone H1 is linked to the surface of an implant or is contained in and released from an implant. Histone H1 is therefore present at the implantation site and inhibits bacterial growth at the implantation site during and after surgery. According to the invention, histone H1 that is linked to the surface of an implant or is contained in and released from an implant mediates long-term protection against the survival, activation and proliferation of bacteria that have unwantedly been introduced into the implantation site.

According to the invention, histone H1 is incorporated into a surgical implant, and is therefore present at the surface of the implant or is released from the implant during and/or after surgery. Histone H1 thus confers antimicrobial protection against the proliferation of unwanted bacteria at the implantation she. An important advantage of the incorporation of histone H1 as bactericidal agent into an implant is in addition, that histone H1 is only weakly immunogenic and does not lead to unwanted immune responses at the implantation site.

In a first embodiment of the invention for the incorporation of histone H1 into sterile materials, surfaces of titanium implants are coated with histone H1. The surface of titanium implants can easily be coated with positively charged histone H1. Because of its oxidation potential, the surface of titanium is always covered by a thin and tightly adherent layer of titanium oxide. In a first step, the oxide layer is treated by chemical procedures of the prior art, in order to contain hydroxyl groups or anionic oxygen groups, that readily bind positively charged histone H1 by electrostatic interaction. In a second step, the titanium implant that contains negative charges on its surface is brought into contact with positively charged histone H1, that readily adheres by electrostatic interaction to the surface of the titanium implant.

In a first preferred embodiment, the titanium implant is in a first step chemically treated with a procedure, selected from the group including but not limited to the procedures of the prior art, to obtain a negatively charged surface of the titanium implant. In a second step, the implant is sterilized with methods of the prior art, e.g. by exposure to heat, and in a third step, the implant is brought into contact with histone H1 in sterile form, e.g. as sterile powder, or as sterile solution, to allow the electrostatic interaction between the negatively charged surface of the titanium implant and the positively charged histone H1. If a sterile powder of histone H1 is used, the coating of the titanium implant with histone H1 and the packaging of the implant can be executed in a single step under sterile conditions. If a sterile solution of histone H1 is used, an additional step of drying and packaging of the histone H1-covered titanium implant under sterile conditions is required. The packed histone H1-coated implant can in addition be sterilized again with ethylene oxide, ionizing radiation such as $\gamma$ radiation or any other sterilization method, other than heat, that does not denature the native biologically active conformation of histone H1.

In a second preferred embodiment, the titanium implant is in a first step chemically treated with a procedure, selected from the group including but not limited to the procedures of the prior art, to obtain a negatively charged surface of the implant. In a second step, the titanium implant is brought into contact with histone H1, e.g. with a solution of histone H1 or a powder containing histone H1, to allow the electrostatic interaction between the negatively charged surface of the titanium implant and the positively charged histone H1. In a third step, the histone H1-coated titanium implant is dried, if necessary, and packaged. In a fourth step, the packaged histone H1-coated implant is sterilized with ethylene oxide, ionizing radiation such as $\gamma$ radiation or any other sterilization method, other than heat, that does not denature the native biologically active conformation of histone H1.

According to still another embodiment of the invention, histone H1 is adhered to the surface of a titanium implant, or an implant of any other material used for surgical implants, e.g. a carbon implant in dental surgery, by a method, including a first step of fixing chosen coupling groups that bind histone H1, e.g. by electrostatic or by covalent binding, to the surface of the implant, wherein said coupling groups are selected from the group including but not limited to coupling groups of the prior art capable of binding histone H1, a second step of binding histone H1 to the implant, wherein histone H1 is bound to the coupling groups on the surface of the implant, and a third step, wherein the histone H1-coated implant is packaged. In a fourth step, the packaged implant is sterilized with ethylene oxide, ionizing radiation such as γ radiation or any other sterilization method, other than heat, that does not denature the native biologically active conformation of histone H1.

In still another embodiment of the invention, the implant, on the surface whereof coupling groups have been fixed in a first step as described above, is sterilized with a chosen method that does not inactivate the coupling groups on the implant and does not interfer with the subsequent binding of histone H1 to said coupling groups. In a further step, the implant is brought into contact with histone H1 in sterile form, e.g. as sterile powder, or in sterile solution, to allow binding of histone H1 to the coupling groups on the surface of the implant, e.g. by electrostatic or by covalent binding. If a sterile powder of histone H1 is used, the coating of the titanium implant with histone H1 and the packaging of the implant can be executed in a single step under sterile conditions. If a sterile solution of histone H1 is used, an additional step of drying and packaging of the histone H1-covered titanium implant under sterile conditions is required. The packed histone H1-coated implant can again be sterilized with ethylene oxide, ionizing radiation such as γ radiation or any other sterilization method, other than heat, that does not denature the native biologically active conformation of histone H1.

According to a preferred embodiment, all of the above-described methods for coating the surface of an implant with histone H1 can be modified, in order to coat only at least one chosen part of the surface of an implant.

According to still another embodiment of the invention, the surface or any chosen part of the surface of an implant is coated with a histone H1-containing layer, that releases histone H1 within the transplantation site in a continuous way over a chosen period of time. The continuous release of histone H1 from the histone H1-containing surface layer confers continuous protection against unwanted bacterial growth over a prolonged period of time. In addition, the amount of histone H1 released in a given period of time and thus the concentration of free histone H1 at the surface of the implant can be chosen, according to the invention.

In a preferred embodiment, the histone H1-containing layer on the surface of the implant is formed of a polymer matrix that contains histone H1, wherein the polymer matrix can take up water and/or is biodegradable. Histone H1 is released from the histone H1-containing layer by diffusion from the polymer matrix and/or by degradation of the polymer matrix. The polymer matrix of the histone H1-containing layer of the implants of the invention is biocompatible and is not toxic. The polymer matrix is pyrrogen-free, and does not cause irritation or inflammation of the tissues at the implantation site. In addition, the polymer matrix is immunologically inert, i.e. it does not lead to a specific or unspecific activation and/or response of the immune system.

The polymer matrix of the histone H1-containing layer of the implants of the invention is chosen from the group including, but not limited to the biocompatible and biodegradable and/or hydratable polymers that are known or are continually developed in the fields of galenics or pharmacology for the continuous release of pharmaceutical compounds within the body, in particular for the long-term release of pharmaceutical compounds from implanted storage devices. Such storage devices are in particular known from or are continuously developed for contraception, or in the treatment of diabetes, or other chronical diseases. In a preferred embodiment, the polymer matrix of the histone H1-containing layer of the implants of the invention is chosen from the polymers that are adapted to contain and/or release positively charged molecules, and in particular positively charged proteins, such as histone H1.

In another preferred embodiment of the invention, long-term catheters are provided that mediate protection against bacterial infection by the bactericidal action of histone H1. Long-term catheters, such as are used e.g. for bypass surgery, i.v. lines, i.v. pumps or urinary catheters often have to be removed from the patient because of local infections. Infections by bacteria or fungi that enter into the body along the surface of catheters or are introduced on the surface of catheters are very frequent with long-term catheters and are a severe problem that leads to local irritation, damage or destruction of tissue, causing continuous suffering of patients with long-term catheters and can in addition lead to systemic infection. In the prior art, the above-mentioned hygienic problems with urinary and blood catheters are an unsolved problem.

In the invention, catheters of any form and for every application are provided that contain histone H1 at their surface or release histone H1 continuously over a chosen period of time and thus confer protection against bacterial infection. The catheters of the invention are chosen from the group containing but not limited to blood catheters, e.g. such as are used for bypass surgery, i.v. lines, i.v. pumps, and urinary catheters.

In a first embodiment, the catheters of the invention are made of the materials for catheters of the prior art and are coated with histone H1 at least on their outer surface. Coating of catheters with histone H1 can be executed by bringing into contact the preformed catheters with histone H1 in solution or in the form of powder, wherein histone H1 is spontaneously adsorbed to the unchanged surface of the catheter. The coated catheters are packaged and sterilized with any method for sterilizing, that does not irreversibly disrupt the biologically active conformation of histone H1.

According to a preferred embodiment, coating of catheters can be enhanced by a chemical, physico-chemical, electrical, or radiation treatment of catheters that confers negative charges to the surface of the catheters. According to another preferred embodiment, coupling groups for histone H1 are fixed to at least the outer surface of the catheters of the invention and histone H1 is bound by electrostatic and/or covalent interactions to at least the outer surface of the catheters. According to another preferred embodiment, catheters are formed of or contain in at least one chosen segment a material that binds with high affinity to histone H1. Said material is chosen from the group including, but not limited to, negatively charged polymers and polymers with coupling groups that interact by electrostatic or covalent interaction with histone H1. According to the invention, histone H1 can be released from coated catheters or remain fixed at the surface of coated catheters.

According to still another preferred embodiment, the catheters of the invention contain a surface layer of a polymer matrix, containing histone H1, wherein the polymer matrix can take up water and/or is biodegradable. Histone H1 is released from the histone H1-containing layer by diffusion from the polymer matrix and/or by degradation of the polymer matrix. The polymer matrix of the histone H1-containing layer of the catheters of the invention is biocompatible and is not toxic, is pyrrogen-free, and does not cause irritation or inflammation of the tissues, that get into contact with the catheter. In addition, the polymer matrix is immunologically inert, i.e. it does not lead to a specific or unspecific activation and/or response of the immune system. The polymer matrix of the histone H1-containing layer of the catheters of the invention is chosen from the group including, but not limited to the biocompatible and biodegradable and/or hydratable polymers that are known or are continually developed in the fields of galenics or pharmacology for the continuous release of pharmaceutical compounds within the body, in particular for the long-term release of pharmaceutical compounds from implanted storage devices. Such storage devices are in particular known from or are continuously developed for contraception, or in the treatment of diabetes, or other chronical diseases. In a preferred embodiment, the polymer matrix of the histone H1-containing layer of the catheters of the invention is chosen from the polymers that are adapted to contain and/or release positively charged molecules, and in particular positively charged proteins, such as histone H1.

According to a further aspect of the invention, band aid, medical wound dressings, plasters, and sanitary napkins and vaginal tampons for the treatment of infections with unwanted bacteria are provided that contain histone H1. In this embodiment, histone H1 can be applied with advantage in the form of powder or in any form of an histone H1-containing impregnation.

According to still another aspect of the invention, wraps of synthetic polymers for the covering and the conservation of food are provided, that contain histone H1 and inhibit the growth of microorganisms. The wraps of synthetic polymers of the invention can be used with advantage for the save storage of perishable food, such as e.g. cheese, meat, and fish.

According to a first embodiment, histone H1 is bound to the wraps of synthetic polymers of the invention by electrostatic interaction. In this case, the synthetic polymer contains or is manipulated to contain negative charges and therefore binds positively charged histone H1. In a second embodiment, histone H1 is covalently linked to anchoring groups of at least one synthetic polymer contained in or forming the wraps of the invention. According to the invention, histone H1 can be linked to either or both of the surfaces of the inventive wrap of synthetic polymer. The wraps of the invention are formed of any synthetic polymer that can bind or can be made to bind histone H1. In a further embodiment, the wraps of synthetic polymers of the invention can on both or either side contain at least one layer of a polymer matrix containing histone H1. In still a further embodiment, histone H1 can be continuously released from the wraps of synthetic polymers and/or from some layer of a polymer matrix on a surface of said wrap of synthetic polymers.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An antimicrobial composition comprising a substantially purified eukaryotic histone H1 protein which exhibits antibiotic activity and interacts with a cell membrane of a microorganism and changes or disrupts the cell membrane, whereby at least one of death of the microorganism and inhibition of growth of the microorganisms is induced, wherein the histone H1 protein is covalently linked with polyethylene glycol.

2. An antimicrobial composition comprising a eukaryotic histone H1 protein which exhibits antibiotic activity and interacts with a cell membrane of a microorganism and changes or disrupts the cell membrane, whereby at least one of death of the microorganism and inhibition of growth of the microorganisms is induced, and further comprising a second antimicrobial composition comprising an antibiotic selected from the group consisting of histone H2A, histone H2B, histone H3, histone H4, histone H5, penicillin, streptomycin, vancomycin, bacitracin, polymyxin, neomycin, chloramphenicol, chlortetracycline, ciprofloxacin, tobramycin, erythromycin, genamicin, gramicidin, oxytetracycline and norfloxacin, wherein any of the penicillin, streptomycin, vancomycin, bacitracin, polymyxin, neomycin, chloramphenicol, chlortetracycline, ciprofloxacin, tobramycin, erythromycin, genamicin, gramicidin, oxytetracycline and norfloxacin is in a form selected from the group consisting of a salt and an ester.

3. An antimicrobial composition comprising a eukaryotic histone H1 protein and lysozyme.

4. The composition of claim 3, wherein the histone H1 protein is substantially purified.

5. The composition of claim 4, wherein the histone H1 protein is covalently linked with polyethylene glycol.

6. The composition of claim 3, further comprising a second antimicrobial composition.

7. The composition of claim 6, wherein the second antimicrobial composition comprises an antibiotic selected from the group consisting of histone H2A, histone H2B, histone H3, histone H4, histone H5, penicillin, streptomycin, vancomycin, bacitracin, polymyxin, neomycin, chloramphenicol, chlortetracycline, ciprofloxacin, tobramycin, erythromycin, genamicin, gramicidin, oxytetracycline and norfloxacin.

8. The composition of claim 7, wherein any of the penicillin, streptomycin, vancomycin, bacitracin, polymyxin, neomycin, chloramphenicol, chlortetracycline, ciprofloxacin, tobramycin, erythromycin, genamicin, gramicidin, oxytetracycline and norfloxacin is in a form selected from the group consisting of a salt and an ester.

9. A kit comprising the composition of claim 8 in the form of a material selected from the group consisting of a tablet, a hard or soft capsule, a cachet, a troche, a lozenge, a powdered formulation, a granular formulation, an aqueous solution, an aqueous suspension, an oily solution, an oily suspension and an emulsion, each material containing a predetermined amount of the histone H1 protein.

10. The kit of claim 9, wherein the composition is included in a wound dressing.

11. A personal care product supplemented with an antimicrobial composition comprising a eukaryotic histone H1 protein.

12. The personal care product of claim 11, wherein the histone H1 protein is substantially purified.

13. The personal care product of claim 12, wherein the histone H1 protein is covalently linked with polyethylene glycol.

14. The personal care product of claim 11, further comprising a second antimicrobial composition.

15. The personal care product of claim 14, wherein the second antimicrobial composition comprises an antibiotic selected from the group consisting of histone H2A, histone H2B, histone H3, histone H4, histone H5, penicillin, streptomycin, vancomycin, bacitracin, polymyxin, neomycin, chloramphenicol, chlortetracycline, ciprofloxacin, tobramycin, erythromycin, genamicin, gramicidin, oxytetracycline and norfloxacin.

16. The personal care product of claim 15, wherein any of the penicillin, streptomycin, vancomycin, bacitracin, polymyxin, neomycin, chloramphenicol, chlortetracycline, ciprofloxacin, tobramycin, erythromycin, genamicin, gramicidin, oxytetracycline and norfloxacin is in a form selected from the group consisting of a salt and an ester.

17. The personal care product of claim 11, selected from the group consisting of a cream, a lotion, a deodorant, a lipstick, a toothpaste, a tooth powder, a dental floss, a mouthwash, a sanitary napkin, a vaginal tampon and an insole.

18. A medical device comprising an antimicrobial composition comprising a eukaryotic histone 1 protein.

19. The medical device of claim 18, wherein the histone H1 protein is substantially purified.

20. The medical device of claim 19, wherein the histone H1 protein is covalently linked with polyethylene glycol.

21. The medical device of claim 18, further comprising a second antimicrobial composition.

22. The medical device of claim 21, wherein the second antimicrobial composition comprises an antibiotic selected from the group consisting of histone H2A, histone H2B, histone H3, histone H4, histone H5, penicillin, streptomycin, vancomycin, bacitracin, polymyxin, neomycin, chloramphenicol, chlortetracycline, ciprofloxacin, tobramycin, erythromycin, genamicin, gramicidin, oxytetracycline and norfloxacin.

23. The medical device of claim 22, wherein any of the penicillin, streptomycin, vancomycin, bacitracin, polymyxin, neomycin, chloramphenicol, chlortetracycline, ciprofloxacin, tobramycin, erythromycin, genamicin, gramicidin, oxytetracycline and norfloxacin is in a form selected from the group consisting of a salt and an ester.

24. The medical device of claim 18 wherein the antimicrobial composition is linked to a surface of the medical device.

25. The medical device of claim 18 wherein the antimicrobial composition is contained in and released from the medical device.

26. The medical device of claim 18, selected from the group consisting of a surgical implant, a catheter, an intravenous pump, a wound dressing, a plaster, a sanitary napkin and a vaginal tampon.

27. The medical device of claim 18, wherein the device is a titanium implant having a portion of its surface chemically modified and comprising histone H1 protein.

28. A medical device of claim 18 comprising a coated surface containing histone H1 protein.

29. A medical device of claim 18 comprising a coupling group on the surface of the device for covalently or electrostatically linking the histone H1 protein to the surface.

30. A medical device of claim 18, wherein the device comprises a coating with a composition comprising the histone H1 protein and at least one of a synthetic polymer and a polymer containing a biological macromolecule.

31. A wrap of synthetic polymer for perishable food, the wrap comprising an antimicrobial composition comprising a eukaryotic histone H1 protein.

32. The wrap of claim 31, wherein the histone H1 protein is substantially purified.

33. The wrap of claim 31, further comprising a second antimicrobial composition.

34. The wrap of claim 33, wherein the second antimicrobial composition comprises an antibiotic selected from the group consisting of histone H2A, histone H2B, histone H3, histone H4, histone H5, penicillin, streptomycin, vancomycin, bacitracin, polymyxin, neomycin, chloramphenicol, chlortetracycline, ciprofloxacin, tobramycin, erythromycin, genamicin, gramicidin, oxytetracycline and norfloxacin.

35. The wrap of claim 34, wherein any of the penicillin, streptomycin, vancomycin, bacitracin, polymyxin, neomycin, chloramphenicol, chlortetracycline, ciprofloxacin, tobramycin, erythromycin, genamicin, gramicidin, oxytetracycline and norfloxacin is in a form selected from the group consisting of a salt and an ester.

36. The wrap of claim 31, wherein the histone H1 protein is covalently linked to anchoring groups of at least one synthetic polymer containing or forming the wrap.

37. The wrap of claim 31 comprising a coupling group on the surface of the wrap covalently-linked with the histone H1 protein.

* * * * *